(12) United States Patent
Shepard

(10) Patent No.: US 6,495,553 B1
(45) Date of Patent: Dec. 17, 2002

(54) METHODS AND COMPOSITIONS FOR OVERCOMING RESISTANCE TO BIOLOGIC AND CHEMOTHERAPY

(75) Inventor: H. Michael Shepard, Rancho Santa Fe, CA (US)

(73) Assignee: NewBiotics, Inc., San Diego, CA (US)

( * ) Notice: Subject to any disclaimer, the term of this patent is extended or adjusted under 35 U.S.C. 154(b) by 0 days.

(21) Appl. No.: 09/130,839

(22) Filed: Aug. 7, 1998

Related U.S. Application Data

(60) Provisional application No. 60/055,525, filed on Aug. 8, 1997.

(51) Int. Cl.⁷ .................. A61K 31/495; A61K 31/505; A61K 31/70; A61K 31/675

(52) U.S. Cl. .................. 514/256; 514/49; 514/50; 514/85; 514/86; 514/247

(58) Field of Search ................ 514/2, 49, 79, 514/85, 50, 86, 183, 247, 256; 435/183, 191

(56) References Cited

U.S. PATENT DOCUMENTS

| | | | |
|---|---|---|---|
| 3,852,266 A | 12/1974 | Kiyanagi et al. | 260/211.5 |
| 4,247,544 A | 1/1981 | Bergstrom et al. | |
| 4,267,171 A | 5/1981 | Bergstrom et al. | |
| 4,542,210 A | 9/1985 | Sakata et al. | |
| 4,816,570 A | 3/1989 | Farquhar | |
| 4,948,882 A | 8/1990 | Ruth | |
| 4,975,278 A | 12/1990 | Senter et al. | |
| 5,070,082 A | 12/1991 | Murdock et al. | 514/105 |
| 5,077,282 A | 12/1991 | Murdock et al. | 514/80 |
| 5,077,283 A | 12/1991 | Murdock et al. | 514/94 |
| 5,085,983 A | 2/1992 | Scanlon | |
| 5,116,827 A | 5/1992 | Murdock et al. | 514/82 |
| 5,212,161 A | 5/1993 | Moriniere et al. | 514/50 |
| 5,212,291 A | 5/1993 | Murdock et al. | 536/6.4 |
| 5,233,031 A | 8/1993 | Borch et al. | |
| 5,264,618 A | 11/1993 | Felgner et al. | |
| 5,457,187 A | 10/1995 | Gmeiner et al. | 536/25.5 |
| 5,459,127 A | 10/1995 | Felgner et al. | |
| 5,521,161 A | 5/1996 | Malley et al. | 514/45 |
| 5,616,564 A | 4/1997 | Rapaport | 514/44 |
| 5,627,165 A | 5/1997 | Glazier | |
| 5,645,988 A | 7/1997 | Vande Woude et al. | |
| 5,798,340 A | 8/1998 | Bischofberger et al. | |
| 5,981,507 A | 11/1999 | Josephson et al. | |

FOREIGN PATENT DOCUMENTS

| | | | |
|---|---|---|---|
| GB | 982776 | | 2/1965 |
| WO | WO 89/05817 | | 6/1989 |
| WO | WO 94/03467 | | 2/1994 |
| WO | WO 94/22483 | | 10/1994 |
| WO | WO 95/01806 | | 1/1995 |
| WO | WO 95/08556 | | 3/1995 |
| WO | WO 96/03151 | | 2/1996 |
| WO | WO 96/07413 | * | 3/1996 |
| WO | WO 96/07413 A1 | | 4/1996 |
| WO | WO 96/10030 | | 4/1996 |
| WO | WO 96/29336 | | 9/1996 |
| WO | WO 96/33168 | | 10/1996 |
| WO | WO 96/40708 | | 12/1996 |
| WO | WO 97/28179 | | 8/1997 |
| WO | WO 99/20741 | | 4/1999 |
| WO | WO 99/23104 | | 5/1999 |

OTHER PUBLICATIONS

European Search Report dated Sep. 11, 2000.

Dagle et al., "Targeted Degradation of mRNA in *Xenopus* oocytes and Embryos Directed by Modified Oligonucleotides: Studies of An2 and Cyclin in Embryogenesis," *Nucleic Acids Research*, 18(16), 4751–4757 (Aug. 25, 1990).

Larsson, P.–A. et al., "Thymidylated Synthase in Advanced Gastrointestinal and Breast Cancers" *Acta Oncologica* 35(4):469–472 (1996).

Hakimelahi et al., "Design, Synthesis, and Structure–Activity Relationship of Novel Dinucleotide Analogs as Agents Against Herpes and Human Immunodeficiency Viruses," *Journal of Medicinal Chemistry*, 38(23), 4648–4659 (Nov. 10, 1995).

Naesens et al., "Anti–HIV Activity and Metabolism of Phosphoramidate Derivatives of D4T–MP with Variations in the Amino Acid Moiety," Poster Session 1, *The Tenth International Conference on Antiviral Research*, Hotel Nikko, Atlanta, GA, Apr. 6–11, 1997; published in *Antiviral Research*, 34(2), p. A54 (Abstract 40), (Apr., 1997).

Ayisi et al., "Comparison of the antiviral effects of 5–methoxymethyldeoxyuridine–5'–monophosphate with adenine arabinoside–5'–monophosphate" *Antiviral Res.* 3:161–174 (1983).

(List continued on next page.)

*Primary Examiner*—Anthony C. Caputa
*Assistant Examiner*—Anne L. Holleran
(74) *Attorney, Agent, or Firm*—Antoinette F. Konski; Bingham McCutchen LLP

(57) ABSTRACT

This invention provides a method for identifying potential therapeutic agents by contacting a target cell with a candidate therapeutic agent which is a selective substrate for an endogenous, intracellular enzyme in the cell which is enhanced in its expression as a result of selection by biologic or chemotherapy. This invention also provides methods and examples of molecules for selectively killing a pathological cell by contacting the cell with a prodrug that is a selective substrate for an endogenous, intracellular enzyme. The prodrug is subsequently converted to a cellular toxin. Further provided by this invention is a method for treating a pathology characterized by pathological, hyperproliferative cells in a subject by administering to the subject a prodrug that is a selective substrate for an endogenous, overexpressed, intracellular enzyme, and converted by the enzyme to a cellular toxin in the hyperproliferative cell.

12 Claims, 5 Drawing Sheets-

OTHER PUBLICATIONS

Goldberg et al., "Novel cell imaging techniques show induction of apoptosis and proliferation in mesothelial cells by asbestos" *Am. J. Respir. Cell Mol. Biol.* 17:265–271 (1997).

Pardo et al., "The incorporation of deoxyuridine monophosphate into DNA increases the sister–ochromatid exchange yield" *Exp. Cell Res.* 168:507–517 (1987).

Collins, J.M. et al., "Suicide Prodrugs Activated by Thymidylate Synthase: Rationale for Treatment and Noninvasive Imaging of Tumors with Deoxyuridine Analogues" *Clin. Cancer Res.* 5:1976–1981 (Aug. 1999).

Katki, A.G. et al., "Prodrugs Activated by Thymidylate Synthase: Treatment of Tumors with Deoxyuridine Analogs" *Proc. Amer. Assoc. Cancer Res. 39*, Abstract No. 1275 (Mar. 1998).

Akdas, A. et al., "Glutathione S–tranferase and multidrug–resistant phenotype in transitional cell carcinoma of the bladder" *Eur. Urol.* 29(4):483–486 (1996).

Almasan, A. et al., "Genetic instability as a consequence of inappropriate entry into and progression through S–phase" *Cancer Metastasis Rev.* 14:59–73 (1995).

Andersen et al., "Detection of c–erbb–2 related protein in sera from breast cancer patients" *Acta Oncol.* 34(4):499–504 (1995).

Antelman, D. et al., "Inhibition of tumor cell proliferation in vitro and in vivo by exogenous $p110^{RB}$, the retinoblastoma tumor suppressor protein" *Oncogene* 10:697–704 (1995).

Balzarini, J. et al., "Thymidylate synthase is the principal target enzyme for the cytostatic activity of (E)–5–(2–bromovinyl)–2'–deoxyuridine against murine mammary carcinoma (FM3A) cells transformed with the herpes simplex virus type 1 or type 2 thymidine kinase gene" *Mol. Pharmacol.* 32:410–416 (1987).

Banerjee, D. et al., "Molecular mechanisms of resistance to antifolates, a review" *Acta Biochem. Pol.* 42(4):457–464 (1995).

Banerjee D. et al., "Role of E2F–1 in chemosensitivity" *Cancer Res.* 58:4292–4296 (1998).

Barbour, K. W. et al., "A naturally occurring tyrosine to histidine replacement at residue 33 of human thymidylate synthase confers resistance to 5–fluoro–2'–deoxyuridine in mammalian and bacterial cells" *Mol. Pharmacol.* 42:242–248 (1992).

Barr, P.J. et al., "Thymidylate synthetase–catalyzed conversions of E–5–(2–Bromovinyl)–2'–deoxyuridylate" *J. Biol. Chem.* 258(22):13627–13631 (1983).

Bergstrom, D. E. et al., "C–5–substituted pyrimidine nucleosides. 3. Reaction of allylic chlorides, alcohols, and acetates with pyrimidine nucleoside derived organopalladium intermediates" *J. Org. Chem.* 46(7):1432–1441 (1981).

Bertino, J. R. et al., "Resistance mechanisms to methotrexate in tumors" *Stem Cells* 14:5–9 (1996).

Bigge, C. F. et al., "Palladium–catalyzed coupling reactions of uracil nucleosides and nucleotides" *J. Amer. Chem. Soc.* 102:2033–2038 (1980).

Bosslet, K. et al., "A novel one–step tumor–selective prodrug activation system" *Tumor Targeting* 1:45–50 (1995).

Bosslet, K. et al., "Elucidation of the mechanism enabling tumor selective prodrug monotherapy" *Cancer Res.* 58:1195–1201 (1998).

Brison, O., "Gene amplification and tumor progression" *Biochem. Biophys. Acta* 1155:25–41 (1993).

Carl, P.L. et al., "Protease–activated 'prodrugs' for cancer chemotherapy" *PNAS USA* 77(4):2224–2228 (1980).

Carreras, C.W. et al., "The catalytic mechanism and structure of thymidylate synthase" *Ann. Rev. Biochem.* 64:721–762 (1995).

Carter, P. et al., "Humanization of an anti–$p185^{HER2}$ antibody for human cancer therapy" *PNAS USA* 89:4285–4289 (1992).

Chen, L. et al., "Sensitization of human breast cancer cells to cyclophosphamide and ifosfamide by transfer of a liver cytochrome P450 gene[1]" *Cancer Res.* 56:1331–1340 (1996).

Clarke, R., "Animal models of breast cancer: Their diversity and role in biomedical research" *Breast Cancer Res. Treat.* 39:1–6 (1996).

Connors, T.A., "Prodrugs in cancer chemotherapy" *Xenobiotica* 16(10/11):975–988 (1986).

Connors, T.A. et al., "Prodrugs in cancer chemotherapy" *Stem Cells* 13:501–511 (1995).

Connors, T.A., "Is there a future for cancer chemotherapy?" *Annals Oncol.* 7:445–452 (1996).

Copur, S. et al., "Thymidylate synthase gene amplification in human colon cancer cell lines resistant to 5–fluorouracil" *Biochem. Pharmacol.* 49(10):1419–1426 (1995).

Dale, R. M. K. et al., "The synthesis and enzymatic polymerization of nucleotides containing mercury: Potential tools for nucleic acid sequencing and structural analysis" *PNAS USA* 70(8):2238–2242 (1973).

Davisson, V.J. et al., "Expression of human thymidylate synthase in *Escherichia coli*" *J. Biol. Chem.* 264(16):9145–9148 (1989).

Davisson, V.J. et al. "Expression of human thymidylate synthase in *Escherichia coli*. (Additions and corrections)" *J. Biol. Chem.* 269(48):30740 (1994).

Dicker, A.P. et al., "Methotrexate resistance in an in vivo mouse tumor due to a non–active–site dihydrofolate reductase mutation" *PNAS USA* 90:11797–11801 (1993).

Dunn, W.J. et al., "Solution of the conformation and alignment tensors for the binding of trimethoprim and its analogs to dihydrofolate reductase: 3D–quantitative structure–activity relationship study using molecular shape analysis, 3–way partial least–squares regression, and 3–way factor analysis" *J. Med. Chem.* 39:4825–4832 (1996).

Eccles, S.A. et al., "Significance of the c–erbB family of receptor tyrosine kinases in metastatic cancer and their potential as targets for immunotherapy" *Invasion Metastasis* 14:337–348 (1995–95).

Eisenbrand, G. et al., "An approach towards more selective anticancer agents" *J. Synthetic Organic Chem.* 10:1246–1258 (1996).

Evrard, A. et al., "An in vitro nucleoside analog screening method for cancer gene therapy" *Cell Biol. Toxicol.* 12:345–350 (1996).

Felip, E. et al., "Overexpression of c–erbB–2 in epithelial ovarian cancer" *Cancer* 75(8):2147–2152 (1995).

Finer–Moore, J. S. et al., "Refined structures of substrate–bound and phosphate–bound thymidylate synthase from *Lactobacillus casei*" *J. Mol. Biol.* 232:1101–1116 (1993).

Finer–Moore, J. S. et al., "Crystal structure of thymidylate synthase from T4 phage: Component of a deoxynucleoside thriphophate–synthesizing complex" *Biochem.* 33:15459–15468 (1994).

Firestone, W. M. et al., "A comparison of the effects of antitumor agents upon normal human epidermal kerarinocytes and human squamos cell carcinoma" *J. Investigative Dermatol.* 94:657–661 (1990).

Fries, K.M. et al., "Synthesis and biological evaluation of 5–fluoro–2'–deoxyuridine phosphoramidate analogs" *J. Med. Chem.* 38(14):2672–2680 (1995).

Garrett, C. et al., "Thymidylate synthetase. Catalysis of dehalogenation of 5–bromo–and 5–iodo–2'–deoxyuridylate" *Biochem.* 18(13):2798–2804 (1979).

Gottesmanm, M.M. et al., "Genetic analysis of the multidrug transporter" *Ann. Rev. Gen.* 29:607–649 (1995).

Gros, P. et al., "Isolation and expression of a complementary DNA that confers mutidrug resistance" *Nature* 323:728–731 (1986).

Gros, P. et al., "Mammalian multidrug resistance gene: Complete cDNA sequence indicates strong homology to bacterial transport proteins" *Cell* 47:371–380 (1986).

Gros, P. et al., "Isolation and characterization of DNA sequences amplified in multidrug–resistant hamster cells" *PNAS USA* 83:337–341 (1986).

Gudkov, A.V. et al., "Cloning and characterization of DNA sequences amplified in multidrug–resistant djungarian hamster and mouse cells" *Somat. Cell Mol. Genet.* 13(6):609–619 (1987).

Hardy, L.W. et al., "Atomic structure of thymidylate synthase: Target for rational drug design" *Science* 235:448–455 (1987).

Harris, M.P. et al., "Adenovirus–mediated p53 gene transfer inhibits growth of tumor cells expressing mutant p53 protein" *Cancer Gene Ther.* 3(2):121–130 (1996).

Hashimoto, Y. et al., "Simple separation of tritiated water and [$^3$H] deoxyuridine from [5–$^3$H] deoxyuridine 5'–monophosphate in the thymidylate synthase assay" *Anal. Biochem.* 167:340–346 (1987).

Hengstchläger, M. et al., "The role of p16 in the E2F–dependent thymidine kinase regulation" *Oncogene* 12:1635–1643 (1996).

Horikoshi, T. et al., "Quantitation of thymidylate synthase, dihydrofoloate reductase, and DT–diaphorase gene expression in human tumors using the polymerase chain reaction" *Cancer Res.* 52:108–116 (1992).

Houze, T.A., "Detection of thymidylate synthase gene expression levels in formalin–fixed paraffin embedded tissue by semiquantitative, nonradioactive reverse transcriptase polymerase chain reaction" *Tumor Biol.* 18:53–68 (1997).

Huang, W.,et al., "Active site general catalysts are not necessary for some proton transfer reactions of thymidylate synthase" *Biochem.* 36:1869–1873 (1997).

Hudziak, R.M. et al., "Amplified expression of the HER2/ERBB2 oncogene induces resistance to tumor necrosis factor α in NIH 3T3 cells" *PNAS USA* 85:5102–5106 (1988).

Hudziak, R.M. et al., "Selection for transformation and met protooncogene amplification in NIH 3T3 fibroblasts using tumor necrosis factor α" *Cell Growth & Differentiation* 1:129–134 (1990).

Jackman, A.L. et al., "Quinazoline–based thymidylate synthase inhibitors: Relationship between structural modifications and polyglutamation" *Anti-cancer Drug Design* 10:573–589 (1995).

Johnston, P.G. et al., "Production and characterization of monoclonal antibodies human thymidylate synthase in the cytoplasm of human cells and tissue" *Cancer Res.* 51:6668–6676 (1991).

Kashani–Sabet, M. et al., "Detection of drug resistance in human tumors by in Vitro enzymatic amplification" *Cancer Res.* 48:5775–5778 (1988).

Klecker, R. W. et al., "Toxicity, metabolism, DNA incorporation with lack of repair, and lactate production for 1–(2'–fluoro–2'–deoxy–βD–arabinofuranosyl)–5–iodouracil in U–937 and MOLT–4 cells" *Mol. Pharmacol.* 46:1204–1209 (1994).

Knighton, E.R. et al., "Structure and kinetic channelling in bifunctional dihydrofolate reductase–thymidylate synthase" *Nature Struct. Biol.* 1(3):186–194 (1994).

Kobayashi, H. et al., "Effect of hammerhead ribozyme against human thymidylate synthase on the cytotoxicity of thymidylate synthase inhibitors" *Jpn. J. Cancer Res.* 86:1014–1018 (1995).

Kumar, A. et al., "Synthesis and Biological Evaluation of Some Cyclic Phosphoramidate Nucleoside Derivatives" *J. Med. Chem.* 33(9):2368–2735 (1990).

Kundu, N.G., "Synthesis and biological activities of [E]–5–(2–acylvinyl) uracils" *Eur. J. Med. Chem.* 28:473–479 (1993).

Lam, K.S., "Application of combinatorial library methods in cancer research and drug discovery" *Anticancer Drug Design* 12:145–167 (1997).

Lasic, D.D., "Doxorubicin in sterically stabilized liposomes" *Nature* 380:561–562 (1996).

Lewis, J.G. et al., "A serum–resistant cytofection for cellular delivery of antisense oligodeoxynucleotides and plasmid DNA" *PNAS USA* 93:3176–3181 (1996).

Li, W. et al., "Lack of functional retinoblastoma protein mediates increased resistance to antimetabolites in human sarcoma cell lines" *PNAS USA* 92:10436–10440 (1995).

Lin, W. et al., "Rhenium–188 hydroxyethylidine diphosphonate: A new generator–produced radiotherapeutic drug of potential value for the treatment of bone metastases" *Eur. J. Nucl. Med.* 24(6):590–595 (1997).

Livingstone, L.R. et al., "Altered cell cycle arrest and gene amplification potential accompany loss of wild–type p53" *Cell* 70:923–935 (1992).

Lönn, U. et al., "Higher frequency of gene amplification in breast cancer patients who received adjuvant chemotherpay" *Cancer* 77(1):107–112 (1996).

Lovejoy, E. et al., "Animal models and the molecular pathology of cancer" *J. Pathol.* 181:130–135 (1997).

Masters, J.N. et al., "The nucleotide sequence of the c DNA coding for the human dihydrofolic acid reductase" *Gene* 21:59–63 (1983).

McGuigan, C. et al., "Certain phosphoramidate derivatives of dideoxy uridine (ddU) are active against HIV and successfully by–pass thymidine kinase" *FEBS Let* 351:11–14 (1994).

McKay, G.A. et al., "Broad spectrum aminoglycoside phosphotransferase type III from Enterococcus: Overexpression, purification, and substrate specificity" *Biochem* 33:6936–6944 (1994).

Meden, H. et al., "Elevated serum levels of a c–erbB–2 oncogene product in ovarian cancer patients and in pregnancy" *J. Cancer Res. Clin. Oncol.* 120:378–381 (1994).

Melton, R.G. et al., "Antibody–enzyme conjugates for cancer therapy" *J. Natl. Cancer Inst.* 88(3/4):153–165 (1996).

Montgomery, J.A. et al., "Phosphonate analogue of 2'–deoxy–5–fluorouridylic acid" *J. Med. Chem.* 22(1):109–111 (1979).

Morgan, A.S. et al., "Tumor efficacy and bone marrow–sparing properties of TER286, a cytotoxin activated by glutathione S–transferase" *Cancer Res.* 58:2568–2575 (1998).

Nakano, T. et al., "Critical role of phenylaline 34 of human dihydrofolate reductase in substrate and inhibitor binding and in catalysis" *Biochem.* 33:9945–9952 (1994).

Nooter, K. et al., "Molecular mechanisms of multidrug resistance in cancer chemotherapy" *Pathol. Res. Pract.* 192:768–780 (1996).

Osaki, M. et al., "5–fluorouracil (5–FU) induced apoptosis in gastric cancer cell lines: Role of the p53 gene" *Apoptosis* 2:221–226 (1997).

Perry, K. M. et al. "Plastic adaptation toward mutations in proteins: Structural comparison of thymidylate synthases" *Proteins* 8:315–333 (1990).

Pestalozzi, B.C. et al., "Prognostic importance of thymidylate synthase expression in early breast cancer" *J. Clin. Oncol.* 15(5):1923–1931 (1997).

Peters, G.J. et al., "Thymidylate synthase and drug resistance" *Eur. J. Cancer* 31A(7/8):1299–1305 (1995).

Pupa, S. M. et al., "The extracellular domain of the c–erbB–2 oncoprotein is released from tumor cells by proteolytic cleavage" *Oncogene* 8:2917–2923 (1993).

Roberts, D., "An isotopic assay for thymidylate synthetase" *Biochem.* 5(11):3546–3548 (1966).

Roninson, I.B. et al., "Amplification of specific DNA sequences correlates with multi–drug resistance in chinese hamster cells" *Nature* 309:626–628 (1984).

Santi, D.V., "Perspectives on the design and biochemical pharmacology of inhibitors of thymidylate synthetase" *J. Med. Chem.* 28(2):103–111 (1980).

Sauter, G. et al., "Heterogeneity of erbB–2 gene amplification in bladder cancer" *Cancer Res.* 53:2199–2203 (1993).

Schiffer, C.A. et al., "Crystal structure of human thymidylate synthase: A structural mechanism for guiding substrates into the active site" *Biochem.* 34:16279–16287 (1995).

Schimke, R.T., "Gene amplification in cultured cells" *J. Biol.Chem.* 263(13):5989–5992 (1988).

Segovia, M., "Leishmania gene amplification: A mechanism of drug resistance" *Annals Tropical Med. Parasitol.* 88(2):123–130 (1994).

Shepard, H. M. et al., "Resistance of tumor cells to tumor necrosis factor" *J. Clin. Immunol.* 8(5):333–341 (1988).

Simon, S.M., "Cell biological mechanisms of multidrug resistance in tumors" *PNAS USA* 91:3497–3504 (1994).

Slamon, D.J. et al., "Human breast cancer: Correlation of relapse and survival with amplification of the HER–2/neu oncogene" *Science* 235:177–182 (1987).

Slamon, D.J. et al., "Studies of the HER–2/neu proto–oncogene in human breast and ovarian cancer" *Science* 244:707–712 (1989).

Smith, K.A. et al., "Regulation and mechanisms of gene amplification" *Phil. Trans. Royal Soc. Lond. B* 347:49–56 (1995).

Snydman, D.R. et al., "Analysis of trends in antimicrobial resistance patterns among clinical isolates of *Bacteriodes fragilis* group species from 1990 to 1994" *Clinical Infectious Disease* 23(Suppl. 1):S54–S65 (1996).

Stühlinger, M. et al., "Clinical therapy and HER–2 oncogene amplification in breast cancer: Chemo–vs radiotherapy" *J. Steroid Biochem. Molec. Biol.* 49(1):39–42 (1994).

Sukumar, S. et al., "Specific patterns of oncogene activation in transplacentally induced tumors" *PNAS USA* 87:718–722 (1990).

Takeishi, K. et al., "Nucleotide sequence of a functional cDNA for human thymidylate synthase" *Nucl. Acid Res.* 13(6):2035–2043 (1985).

Tannock, I.F., "Treatment of cancer with radiation and drugs" *J. Clin. Oncol.* 14(12):3156–3174 (1996).

Troutner, D.E., "Chemical and physical properties of radionuclides" *Nucl. Med. Biol.* 14(3):171–176 (1987).

Ubeda, M. et al., "The large subunit of the DNA replication complex C (DSEB/RF–C140) cleaved and inactivated by caspace–3 (CPP32/YAMA) during fas–induced apoptosis" *J. Biol. Chem.* 272(31):19562–19568 (1997).

Van de Vijver, M. et al., "Amplification of the neu (c–erbB–2) oncogene in human mammary tumors is relatively frequent and is often accompanied by amplification of the linked c–erbA oncogene" *Mol. Cell. Biol.* 7(5):2019–2023 (1987).

Volm et al., "Relationship of inherent resistance to doxorubicin, proliferative activity and expression of P–glycoprotein 170, and glutathione S–transferase–π in human lung tumors" *Cancer* 70(4):764–769 (1992).

Wang, S. et al., "Identification and characterization of Ich–3, a member of te interleukin–1β converting enzyme (ICE)/Ced–3 family and an upstream regulator of ICE" *J. Biol. Chem.* 271(34):20580–20587 (1996).

Wataya, Y. et al., "Trans–5–(3,3,3–trifluoro–1–propenyl)–2'–deoxyuridylate: A mechanism–based inhibitor of thymidylate synthetase" *J. Med. Chem.* 22(4):339–340 (1979).

Wettergren, Y. et al., "Drug–specific rearrangements of chromosome 12 in hydroxyurea–resistant mouse SEWA cells: Support for chromosomal breakage model of gene amplification" *Somatic Cell Mol. Genet.* 20(4):267–285 (1994).

Yen, Y. et al., "Characterization of a hydroxyurea–resistant human KB cell line with supersensitivity to 6–thioguanine[1]" *Cancer Res.* 54:3686–3691 (1994).

Yin, T. et al., "Wild–type p53 restores cell cycle control and inhibits gene amplification in cells with mutant p53 alleles" *Cell* 70:937–948 (1992).

Zhou, Q. et al., "Target protease specificity of the viral serpin CrmA" *J. of Biol. Chem.* 272(12):7797–7800 (1997).

* cited by examiner

METHODS AND COMPOSITIONS FOR OVERCOMING RESISTANCE TO BIOLOGIC AND CHEMOTHERAPY

CROSS-REFERENCE TO RELATED APPLICATIONS

This application claims priority of U.S. provisional application No. 60/055,525, filed Aug. 8, 1997.

TECHNICAL FIELD

The present invention relates to the field of drug discovery and specifically, the design of prodrugs which are substrates for an intracellular enzyme critical to resistance to cancer therapeutics in pathological cells and converted to a cell toxin by the intracellular enzyme.

BACKGROUND

Throughout this disclosure, various publications are referenced by first author and date, patent number or publication number. The full bibliographic citation for each reference can be found at the end of this application, immediately preceding the claims. The disclosures of these references are hereby incorporated by reference into this disclosure to more fully describe the state of the art to which this invention pertains.

Cancer cells are characterized by uncontrolled growth, de-differentiation and genetic instability. The instability expresses itself as aberrant chromosome number, chromosome deletions, rearrangements, loss or duplication beyond the normal dipoid number. Wilson, J. D. et al. (1991). This genomic instability may be caused by several factors. One of the best characterized is the enhanced genomic plasticity which occurs upon loss of tumor suppression gene function (e.g., Almasan, A. et al. (1995)). The genomic plasticity lends itself to adaptability of tumor cells to their changing environment, and may allow for the more frequent mutation, amplification of genes, and the formation of extrachromosomal elements (Smith, K. A. et al. (1995) and Wilson, J. D. et al. (1991)). These characteristics provide for mechanisms resulting in more aggressive malignancy because it allows the tumors to rapidly develop resistance to natural host defense mechanisms, biologic therapies (Wilson, J. D. et al. (1991) and Shepard, H. M. et al. (1988)), as well as to chemotherapeutics. Almasan, A. et al. (1995) and Wilson, J. D. et al. (1991).

Cancer is one of the most commonly fatal human diseases worldwide. Treatment with anticancer drugs is an option of steadily increasing importance, especially for systemic malignancies or for metastatic cancers which have passed the state of surgical curability. Unfortunately, the subset of human cancer types that are amenable to curative treatment today is still rather small (Haskell, C. M. eds. (1995), p. 32). Progress in the development of drugs that can cure human cancer is slow. The heterogeneity of malignant tumors with respect to their genetics, biology and biochemistry as well as primary or treatment-induced resistance to therapy mitigate against curative treatment. Moreover, many anticancer drugs display only a low degree of selectivity, causing often severe or even life threatening toxic side effects, thus preventing the, application of doses high enough to kill all cancer cells. Searching for anti-neoplastic agents with improved selectivity to treatment-resistant pathological, malignant cells remains therefore a central task for drug development. In addition, widespread resistance to antibiotics is becoming an important, world-wide, health issue, Segovia, M. (1994) and Snydman, D. R. et al. (1996).

Classes of Chemotherapeutic Agents

The major classes of agents include the alkylating agents, antitumor antibiotics, plant alkaloids, antimetabolites, hormonal agonists and antagonists, and a variety of miscellaneous agents. See Haskell, C. M., ed., (1995) and Dorr, R. T. and Von Hoff, D. D., eds. (1994).

The classic alkylating agents are highly reactive compounds that have the ability to substitute alkyl groups for the hydrogen atoms of certain organic compounds. Alkylation of nucleic acids, primarily DNA, is the critical cytotoxic action for most of these compounds. The damage they cause interferes with DNA replication and RNA transcription. The classic alkylating agents include mechlorethamine, chlorambucil, melphalan, cyclophosphamide, ifosfamide, thiotepa and busulfan. A number of nonclassic alkylating agents also damage DNA and proteins, but through diverse and complex mechanisms, such as methylation or chloroethylation, flat differ from the classic alkylators. The nonclassic alkylating agents include dacarbazine, carnustine, lomustine, cisplatin, carboplatin, procarbazine and altretamine.

The clinically useful antitumor drugs are natural products of various strains of the soil fungus Streptomyces. They produce their tumoricidal effects by one or more mechanisms. All of the antibiotics are capable of binding DNA, usually by intercalation, with subsequent unwinding of the helix. This distortion impairs the ability of the DNA to serve as a template for DNA synthesis, RNA synthesis, or both. These drugs may also damage DNA by the formation of free radicals and the chelation of important metal ions. They may also act as inhibitors of topoisomerase II, an enzyme critical to cell division. Drugs of this class include doxorubicin (Adriamycin), daunorubicin, idarubicin, mitoxantrone, bleomycin, dactinomycin, mitomycin C, plicamycin and streptozocin.

Plants have provided some of the most useful antineoplastic agents. Three groups of agents from this class are the Vinca alkaloids (vincristine and vinblastine), the epipodophyllotoxins (etoposide and teniposide) and paclitaxel (Taxol). The Vinca alkaloids bind to microtubular proteins found in dividing cells and the nervous system. This binding alters the dynamics of tubulin addition and loss at the ends of mitotic spindles, resulting ultimately in mitotic arrest. Similar proteins make up an important part of nervous tissue; therefore, these agents are neurotoxic. The epipodophyllotoxins inhibit topoisomerase II and therefore have profound effects on cell function. Paclitaxel has complex effects on microtubules.

The antimelabolites are structural analogs of normal metabolites that are required for cell function and replication. They typically work by interacting with cellular enzymes. Among the many antimetabolites that have been developed and clinically tested are methotrexate, 5-fluorouracil (5-FU), floxuridine (FUDR), cytarabine, 6-mercaptopurine (6-MP), 6-thioguanine, deoxycoformycin, fludarabine, 2-chlorodeoxyadenosine, and hydroxyurea.

Endocrine manipulation is an effective therapy for several forms of neoplastic disease. A wide variety of hormones and hormone antagonists have been developed for potential use in oncology. Examples of available hormonal agents are diethylstilbestrol, tumoxifen, megestrol acetate, dexamethasone, prednisone, aminoglutethimide, leuprolide, goserelin, flutamide, and octreotide acetate.

Drawbacks of Current Chemotherapeutic Agents

Among the problems currently associated with the use of chemotherapeutic agents to treat cancers are the high doses of agent required; toxicity toward normal cells, i.e., lack of selectivity; immunosuppression; second malignancies; and drug resistance.

The majority of the agents that are now used in cancer chemotherapy act by an anti-proliferative mechanism. However, most human solid cancers do not have a high proportion of cells that are rapidly proliferating and they are therefore not particularly sensitive to this class of agent. Moreover, most antineoplastic agents have steep dose-response curves. Because of host toxicity, treatment has to be discontinued at dose levels that are well below the dose that would be required to kill all viable tumor cells.

Another side effect associated with present day therapies is the toxic effect of the chemotherapeutic on the normal host tissues that are the most rapidly dividing, such as the bone marrow, gut mucosa and cells of the lymphoid system. The agents also exert a variety of other adverse effects, including neurotoxicity; negative effects on sexuality and gonadal function; and cardiac, pulmonary, pancreatic and hepatic toxicities; vascular and hypersensitivity reactions, and dermatological reactions.

Hematologic toxicity is the most dangerous form of toxicity for many of the antineoplastic drugs used in clinical practice. Its most common form is neutropenia, with an attendant high risk of infection, although thrombocytopenia and bleeding may also occur and be life threatening. Chemotherapy may also induce qualitative defects in the function of both polymorphonuclear leukocytes and platelets. The hematopoietic growth factors have been developed to address these important side effects. Wilson, J. D. et al. (1991) and Dorr, R. T. and Von Hoff, D. D., eds. (1994).

Most of the commonly used antineoplastic agents are capable of suppressing both cellular and humoral immunity. Infections commonly lead to the death of patients with advanced cancer, and impaired immunity may contribute to such deaths. Chronic, delayed immunosuppression may also result from cancer chemotherapy.

The major forms of neurotoxicity are arachnoiditis; myelopathy or encephalomyelopathy; chronic encephalopathies and the somnolence syndrome; acute encephalopathies; peripheral neuropathies; and acute cerebellar syndromes or ataxia.

Many of the commonly employed antineoplastic agents are mutagenic as well as teratogenic. Some, including procarbazine and the alkylating agents, are clearly carcinogenic. This carcinogenic potential is primarily seen as delayed acute leukemia in patients treated with polyfunctional alkylating agents and inhibitors of topoisomerase II, such as etoposide and the anthracycline antibiotics. Chemotherapy has also been associated with cases of delayed non-Hodgkin's lymphoma and solid tumors. The present invention will minimize these effects since the prodrug will only be activated within tumor cells.

The clinical usefulness of a chemotherapeutic agent may be severely limited by the emergence of malignant cells resistant to that drug. A number of cellular mechanisms are probably involved in drug resistance, e.g., altered metabolism of the drugs, impermeability of the cell to the active compound or accelerated drug elimination from the cell, altered specificity of an inhibited enzyme, increased production of a target molecule, increased repair of cytotoxic lesions, or the bypassing of an inhibited reaction by alternative biochemical pathways. In some cases, resistance to one drug may confer resistance to other, biochemically distinct drugs. Amplification of certain genes is involved in resistance to biologic and chemotherapy. Amplification of the gene encoding dihydrofolate reductase is related to resistance to methotrexate, while amplification of the gene encoding thymidylate synthase is related to resistance to treatment with 5-fluoropyrimidines. Table 1 summarizes some prominent enzymes in resistance to biologic and chemotherapy.

TABLE 1

Enzymes Overexpressed in Resistance to Chemotherapy

| Enzyme | Biologic or Chemotherapy | Referenced (Examples) |
|---|---|---|
| Thymidylate synthase | Uracil-based | Lönn, U. et al. |
|  | Folate-based | Kobayashi, H. et al. |
|  | Quinazoline-based | Jackman, AL et al. |
| Dihydrofolate reductase | Folate-based | Banerjee, D. et al. |
|  |  | Bertino, J.R. et al. |
| Tyrosine kinases | TNF-alpha | Hudziak, R.M. et al. |
|  | Multidrug resistance | Stühlinger, M. et al. |
| MDR-associated proteins (ABC P-gp proteins) | Multidrug resistance | Simon, S.M. and Schindler, M. Gottesman, M.M. et al. |
| CAD* | PALLA** | Smith, K.A. et al. |
|  |  | Dorr, R.T. and Von Hoff, D.D., eds. |
| Ribonucleotide reductase | Hydroxyurea | Wettergren, Y. et al. |
|  |  | Yen, Y. et al. |

*CAD = carbamyl-P synthase, aspartate transcarbamylase, dihydroorotase
**PALA = N-(phosphonacetyl)-L-aspartate Use of Prodrugs as a Solution to Enhance Selectivity of a Chemotherapeutic Agent The poor selectivity of anticancer agents has been recognized for a long time and attempts to improve selectivity and allow greater doses to be administered have been numerous. One approach has been the development of prodrugs. Prodrugs are compounds that are toxicologically inert but which may be converted in vivo to active toxic products. In some cases, the activation occurs through the action of a non-endogenous enzyme delivered to the target cell by antibody ("ADEPT" or antibody-dependent enzyme prodrug therapy (U.S. Pat. No. 4,975,278)) or gene targeting ("GDEPT" or gene dependent enzyme-prodrug therapy (Melton, R. G. and Sherwood, R. F. (1996)). These technologies have severe limitations with respect to their ability to exit the blood and penetrate tumors. Connors, T. A. and Knox, R. J. (1995).

Accordingly, there is a need for more selective agents which can penetrate the tumor and inhibit the proliferation and/or kill cancer cells that have developed resistance to therapy. The present invention satisfies this need and provides related advantages as well.

SUMMARY OF THE INVENTION

This invention provides a method for identifying potential therapeutic agents by contacting a target or test cell with a candidate therapeutic agent or prodrug which is a selective substrate for a target enzyme in the cell. In one embodiment, the target enzyme is an endogonous, intracellular enzyme which is overexpressed and confers resistance to biologic and chemotherapeutic agents. In a separate embodiment, the activity of the enzyme has been greatly enhanced in a tumor cell as a result of loss of tumor suppressor function (Smith, K. A. et al. (1995) and Li, W. et al. (1995)) and/or selection resulting from previous exposure to chemotherapy, (Melton, R. G. and Sherwood, R. F. (1996)). In a separate embodiment, the target enzyme is an expression product of a foreign gene in the cell, wherein the foreign gene encodes a target enzyme.

After the cell is contacted in vitro and/or in vivo with the candidate prodrug, the cell is assayed for efficacy of the agent by noting if the agent caused a reduction in cellular proliferation or if the agent kills the cell. In one aspect of this invention, the prodrug kills the cell or inhibits the cellular proliferation by the release of a toxic byproduct from the prodrug by the target enzyme. In a further aspect of this invention, one or more "target enzymes" can be used to activate the prodrug so that it releases the toxic byproduct.

Another aspect of this invention includes kits for use in assaying for new prodrugs having the characteristics described herein against target enzymes. The kits comprise the reagents and instructions necessary to complete the assay and analyze the results.

This invention also provides methods and examples of molecules for selectively killing a pathological cell by contacting the cell with a prodrug that is a selective substrate for a target enzyme, e.g., an endogenous, intracellular enzyme as defined above. The substrate is specifically converted to a cellular toxin by the intracellular target enzyme. In another aspect of this invention, the product of an initial prepatory reaction is subsequently activated by a common cellular enzyme such as an acylase, phosphatase or other "housekeeping" enzyme. Voet, et al. (1995) to release the toxic byproduct from the prodrug.

Further provided by this invention is a method for treating a pathology characterized by pathological, hyperproliferative cells in a subject by administering to the subject a prodrug that is a selective substrate for a target enzyme, and selectively converted by the enzyme to a cellular toxin in the hyperproliferative cell. The prodrugs of this invention may be used alone or in combination with other chemotherapeutics or alternative anti-cancer therapies such as radiation.

A further aspect of this invention is the preparation of a medicament for use in treating a pathology characterized by pathological, hyperproliferative cells in a subject by administering to the subject a prodrug that is a selective substrate for a target enzyme, and selectively converted by the enzyme to a cellular toxin in the hyperproliferative cell.

DETAILED DESCRIPTION OF THE INVENTION

Figure 1:
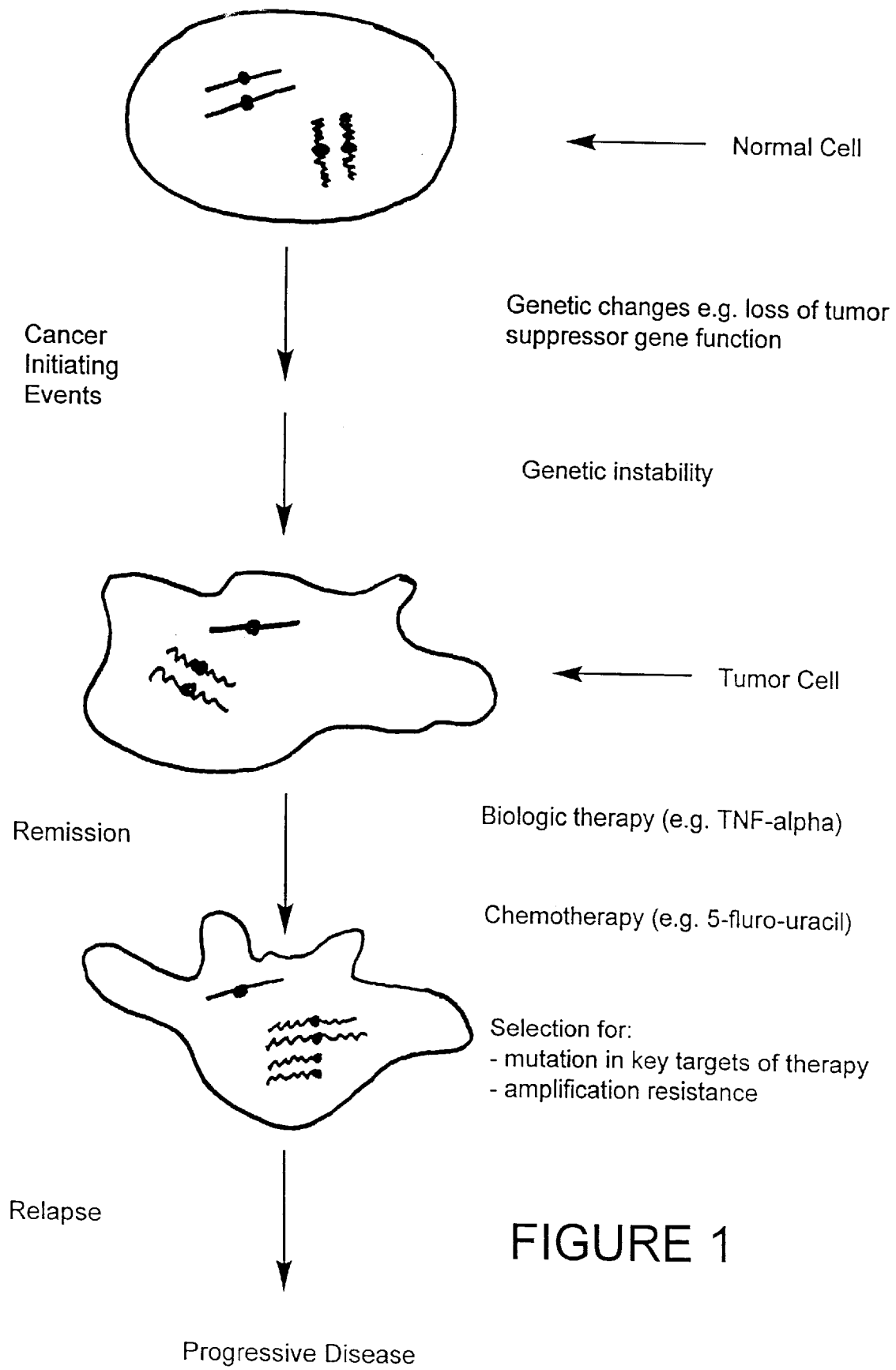
FIG. 1 shows the development of resistance to anti-cancer modalities in cells, and the consequences.
Figure 2:
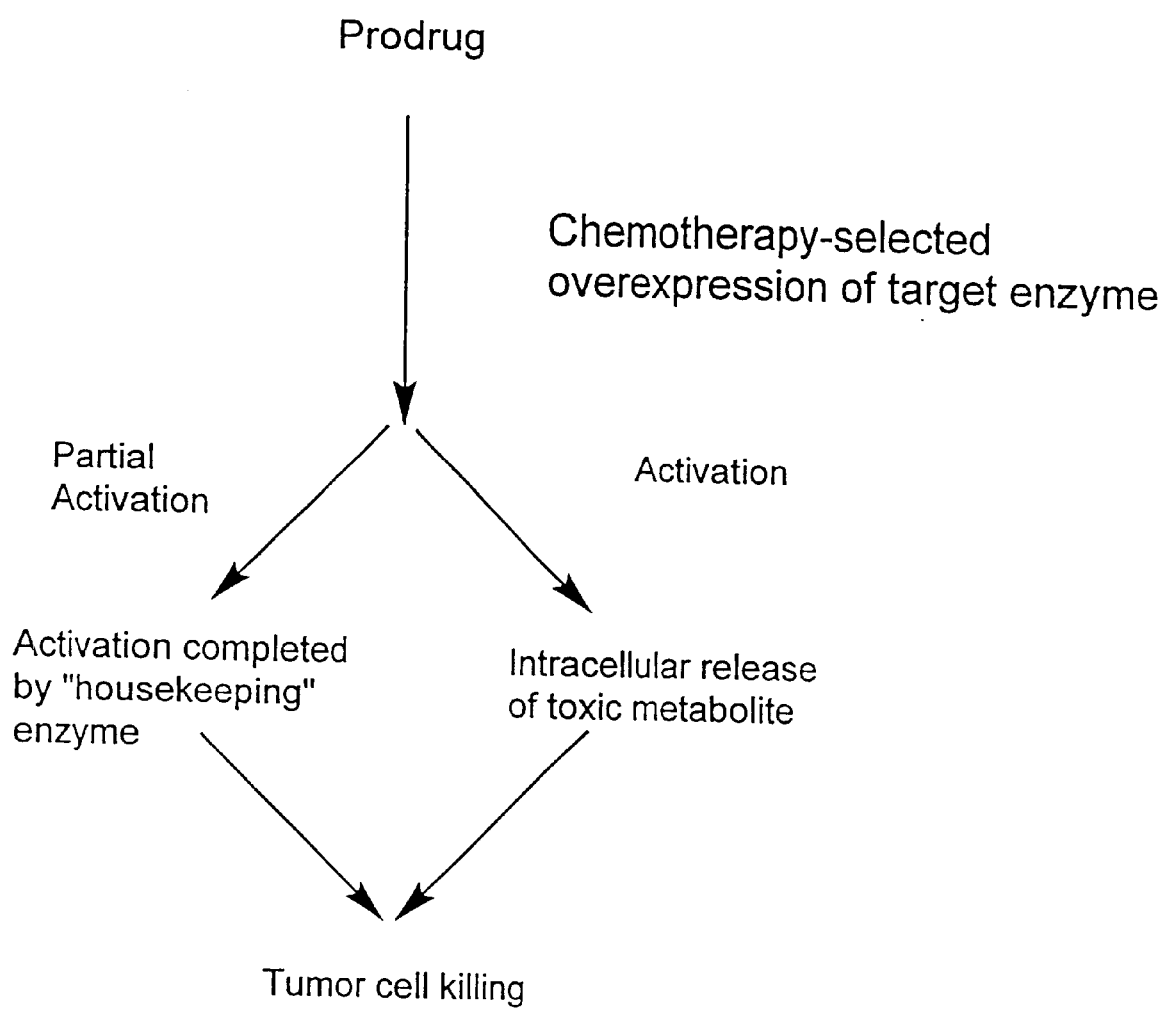
FIG. 2 schematically shows activation pathways of the prodrugs of this invention.

The invention is achieved by exploiting some of the key genomic and phenotypic changes intimately linked to resistance to biologic and chemotherapy of cancer cells. The invention provides a means for in vivo selectively inhibiting the growth and/or killing of cells which have undergone selection by exposure to cancer therapy (including biologic therapy such as tumor necrosis factor (TNF) or chemotherapy). (Refer to Table 1). As a result, certain enzymes which have been activated by mutation or gene amplification are resistant to further therapy by the agent. Unlike prior art therapies directed to creating more potent inhibitors of endogenous, intracellular enzymes, this invention exploits the higher enzyme activity associated with therapy-resistant diseased cells and tissues versus normal cells and tissues and does not rely on inhibiting the enzyme. In one aspect, the tumor cells successfully treated by the prodrugs of this invention are characterized by enhanced target enzyme activity and therefore have a much higher potential to convert the prodrug to its toxic form than do normal cells which do not overexpress the target enzyme. The term "target enzyme" is used herein to define enzymes having one or more of the above noted characteristics.

As used herein, the terms "host cells, "target cells" and "hyperproliferative cells" encompass cells characterized by the activation by genetic mutation or the endogenous overexpression of an intracellular enzyme. In some embodiments, the overexpression of the enzymes is related to drug resistance or the genetic instability associated with a pathological phenotype. A number of cellular mechanisms are involved in drug resistance, e.g., altered metabolism of the drug, impermeability of the cell with regard to the active compound or accelerated drug elimination from the cell, altered specificity of an inhibited enzyme, increased production of a target molecule, increased repair of cytotoxic lesions, or the bypassing of an inhibited reaction by alternative biochemical pathways. Enzymes activated or overexpressed and related to drug resistance include, but are not limited to thymidylate synthase (TS) (Lönn, U. et al. (1996); Kobayashi, H. et al. (1995); Jackman, A. L. et al. (1995)), dihydrofolate reductase (Banerjee, D. et al. (1995) and Bertino, J. R. et al. (1996)), tyrosine kinases (TNF-α, Hudziak, R. M. et al. (1988)) and multidrug resistance (St ühlinger, M. et al. (1994)); Akdas, A. et al. (1996); and (Tannock, I. F. (1996)); and ATP-dependent multidrug resistance associated proteins (Simon, S. M. and Schindler, M. (1994)). Alternatively, resistance to one drug may confer resistance to other, biochemically distinct drugs. While this application is specifically directed to cancer, a similar approach can be applied to enzymes encoded by human and animal pathogens, and in which the inhibitors have failed due to development of resistance.

Amplification of certain genes is involved in resistance to chemotherapy. Amplification of dihydrofolate reductase (DHFR) is related to resistance to methotrexate while amplification of the gene encoding thymidylate synthase is related to resistance to tumor treatment with 5-fluoropyrimidines. Amplification of genes associated with drug resistance can be detected and monitored by a modified polymerase chain reaction (PCR) as described in Kashini-Sabet, et al. (1988) or U.S. Pat. No. 5.085,983. Acquired drug resistance can be monitored by the detection of cytogenetic abnormalities, such as homogeneous chromosome staining regions and double minute chromosomes both of which are associated with gene amplification. Alternative assays include direct or indirect enzyme activity assays and both of which are associated with gene amplification (e.g., Carreras & Santi (1995)); other methodologies (e.g. polymerase chain reaction, Houze, T. A. et al. (1997) or immunohistochemistry (Johnson, P. G. et al. (1997)).

Alternatively, the target cell is characterized as having inactivated tumor suppressor function, e.g. loss or inactivation of retinoblastoma (RB) or p53, known to enhance expression of TS (Li, W. et al. (1995)) or DHFR (Bertino, et al. (1996) and Li, W. et al. (1995)).

The prodrugs of this invention are useful to treat or ameliorate any disease wherein the disease-associated enzyme is associated with drug resistance to a chemotherapeutic and in some embodiments, where the enzyme is overexpressed, over-accumulated or activated in pathological cells versus normal cells, for example, the TS enzyme. Particularly excluded is the enzyme glutathione-S-transferase which has been shown to be elevated in some human tumors. Morgan, A. S. et al. (1998). The prodrugs of the subject invention are distinguishable on the basis that the target enzymes of this invention are commonly overexpressed, overaccumulated or activated in pathological cells versus normal cells. The most important principle which distinguishes the current invention from other approaches are:

(1) This invention describes the synthesis of substrates for enzymes like thymidylate synthase. The overexpressed enzyme will generate toxin, preferentially in diseased cells. Previous approaches have relied on inhibitor. The inhibitors lead to amplified expression of the enzyme, and subsequent resistance to treatment (see, e.g., Lonn, U. et al. (1996).

(2) The current approach is also distinguishable from other "substrate-prodrug" approaches, e.g., the glutathione-S-transferase enzymes (see, e.g., Morgan, A. S. et al. (1998). The enzymes of the GST family are expressed at increased levels in response to toxic insult to the cell. The GST family of enzymes have overlapping substrate specificities, which makes it impossible to design a substrate reactive with only a single species of enzyme with elevated expression in a cancer cell (Morgan, A. S. et al. (1998)). Because each of the enzymes of the current invention (e.g., thymidylate synthase, dihydrofolate reductase and thymidine kinase) is unique with respect to its structure and substrate specificity, it is facile to design unique substrates. Several examples of substrates for thymidylate synthase are provided in the specifications of this application.

(3) In some cases the gene encoding the target enzyme (e.g., thymidylate synthase) may have undergone mutation to give resistance to inhibitors, but will still be capable of carrying out reaction with non-inhibitor substrates. Barbour, K. W. et al. (1992) and Dicken, A. P. et al. (1993).

Drug Assay

This invention provides a method for identifying agents which have therapeutic potential for the treatment of hyperproliferative or neoplastic disorders, e.g., cancer. The method also identifies agents that inhibit the growth of cells or cell cycling of hyperproliferative cells, such as cancer cells. Other cells that are included are bacterial, yeast and parasitic cells which cause disease as a result of inappropriate proliferation in the patient. The agent is considered a potential therapeutic agent if cell proliferation, replication or cell cycling is reduced relative to the cells in a control sample. Most preferably, the cells are killed by the agent. The cells can be procaryotic (bacterial such as *E. coli*) or eucaryotic. The cells can be mammalian or non-mammalian cells, e.g., mouse cells, rat cells, human cells, fungi (e.g., yeast) or parasites (e.g., Pneumocystis or Leishmania) which cause disease.

As used herein, a "hyperproliferative cell" is intended to include cells that are de-differentiated, immortalized, neoplastic, malignant, metastatic or transformed. Examples of such cells include, but are not limited to a sarcoma cell, a leukemia cell, a carcinoma cell, or all adenocarcinoma cell. More specifically, the cell can be a breast cancer cell, a hepatoma cell, a colorectal cancer cell, pancreatic carcinoma cell, an oesophageal carcinoma cell, a bladder cancer cell, an ovarian cancer cell, a skin cancer cell, a liver carcinoma cell, or a gastric cancer cell. In an alternative embodiment, the target cell can be resistant to a drug or compound used to prevent or kill a cell infected with an infectious agent which is resistant to coventional antibiotics. Infectious agents include bacteria, yeast and parasites, such as trypanosomes.

Specific examples of target enzymes that are the subject matter of this invention are listed in Table 1 (above) or Table 2 (below). These enzymes are involved in resistance to chemotherapy, are endogeneously activated, overexpressed or over-accumulated in a cell characterized by resistance to cancer therapy and associated with a pathological or disease include, but are not limited to enzymes such as a member of the tyrosine kinase superfamily or an ATP-dependent MDR-associated protein, CAD, thymidylate synthase, dihydrofolate reductase, and ribonucleotide reductase. Table 2 provides a list of enzymes which may be targeted by this approach in infectious disease.

TABLE 2

Enzymes Overexpressed in infectious disease, and which contribute to drug resistance

| Enzyme | Provides increased Resistance to: |
| --- | --- |
| Beta-lactamases | Penicillin and other beta-lactam containing antibiotics |
| Aminoglycosidase, or aminoglycoside midifying enzymes | Aminoglycoside antibiotics (e.g., streptomycin, gentamycin) |
| Chloramphenicol transacetylase | Chloramphenicol |
| Trimethoprim | Dihydrofolate reductase |

Reference: Mechanisms of Microbial Disease, 2$^{nd}$ Ed., M. Schaechter, G. Medloff, B.I. Eisenstein, Editor TS Satterfield. Publ. Williams and Wilkins, pp. 973 (1993).

The potentially therapeutic agent identified by the method of this invention is a prodrug that is a substrate for the enzyme and is converted intracellularly to an intracellular toxin. As used herein, a "prodrug" is a precursor or derivative form of a pharmaceutically active agent or substance that is less cytotoxic to target or hyperproliferative cells as compared to the drug metabolite and is capable of being enzymatically activated or converted into the more active form (see Connors, T. A. (1986) and Connors, T. A. (1996)). The toxicity of the agent is directed to cells that are producing the converting enzyme in an amount effective to produce a therapeutic concentration of the cellular toxin in the diseased cell.

Figure 3:
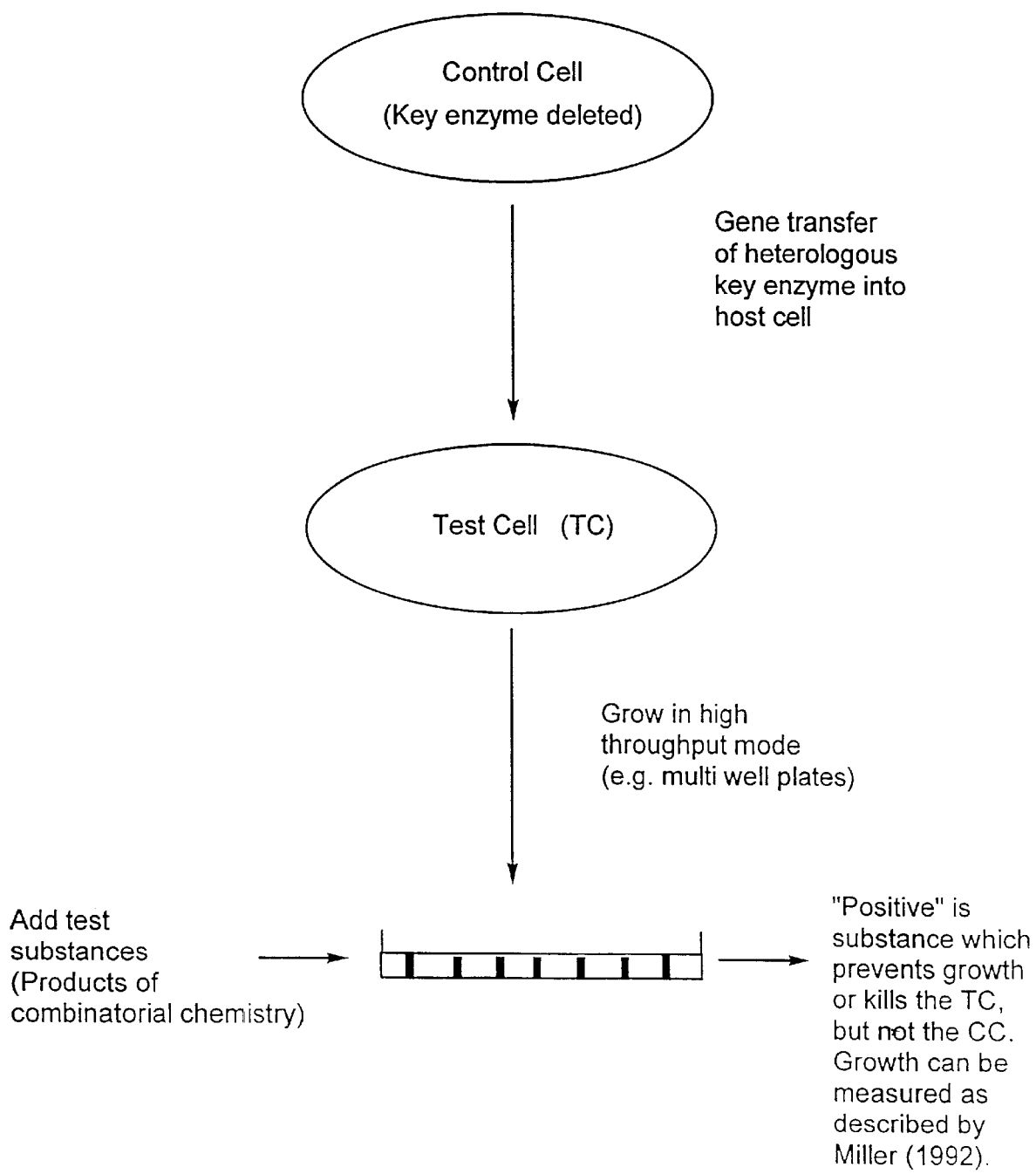
FIG. 3 schematically shows the High Throughput Screen for prodrugs activated by intracellular enzymes important in drug resistance.

This invention also provides a quick and simple screening assay that will enable initial identification of compounds with at least some of the desired characteristics. For purposes of this current invention, the general scheme of one embodiment is shown in FIG. 3. This drawing describes how the assay is arranged and the materials necessary for its process. As shown in FIG. 3, the assay requires two cell types, the first being a control cell in which the target enzyme is not expressed, or is expressed at a low level, The second cell type is the test cell, in which the target enzyme is expressed at a detectable level, e.g., a high level For example, a procaryotic *E. coli* which does not endogenously express the target enzyme TS is a suitable host cell or target cell. The cell can have a control counterpart (lacking the target enzyme), or in a separate embodiment, a counterpart genetically modified to differentially express the target enzyme, or enzymes (containing the appropriate species of target enzyme). More than one species of enzyme can be used to separately tranduce separate host cells, so that the effect of the candidate drug on a target enzyme can be simultaneously compared to its effect on another enzyme or a corresponding enzyme from another species.

In another embodiment, transformed cell lines, such as ras-transformed NIH 3T3 cells (ATCC, 10801 University Blvd., Manassas, Va. 20110-2209, U.S.A.) are engineered to express variable and increasing quantities of the target enzyme of interest from cloned cDNA coding for the enzyme. Transfection is either transient or permanent using procedures well known in the art and described in Chen, L. et al. (1996), Hudziak, R. M. et al. (1988), or Carter, P. et al. (1992). Suitable vectors for insertion of the cDNA are commercially available from Stratagene, La Jolla, Calif. and other vendors. The level of expression of enzyme in each transfected cell line can be monitored by immunoblot and enzyme assay in cell lysates, using monoclonal or polyclonal antibody previously raised against the enzyme for immunodetection. See, e.g., as described by Chen, L. et al. (1996). The amount of expression can be regulated by the number of copies of the expression cassette introduced into the cell or by varying promoter usage. Enzymatic assays also can be performed as reviewed by Carreras, C. W. and Santi, D. V. (1995).

As noted above, cells containing the desired genetic deficiencies may be obtained from Cold Spring Harbor, the Agricultural Research Service Culture Collection, or the American Type Culture Collection. The appropriate strains can also be prepared by inserting into the cell a gene coding for the target enzyme using standard techniques as described in Miller (1992), Sambrook, et al. (1989), and Spector, et al. (1997). Growth assays can be performed by standard methods as described by Miller (1992) and Spector, et al. (1997).

It should be understood by those skilled in the art that the screen shown in FIG. 3 can be applied broadly for the discovery of antibiotics. For example, thymidylate synthase from yeast could be substituted for that of *E. coli* in FIG. 4. This would allow the discovery of specific antifungal antibiotics targeting yeast related pathogens. In addition, other enzymes can be subjected to this treatment. For example, prodrugs which target specifically the dihydrofolate reductase activity of infectious agents, like *Pneumocystis carnii*, could be selected. These agents will be selected for specificity for the target enzyme, and can be shown not to activate the enzyme of the natural host by employing the screening assay described in FIG. 3. The control cellular constructs would contain the corresponding normal human enzyme, in order to show lack of toxicity when only the normal human enzyme is present.

Figure 4:
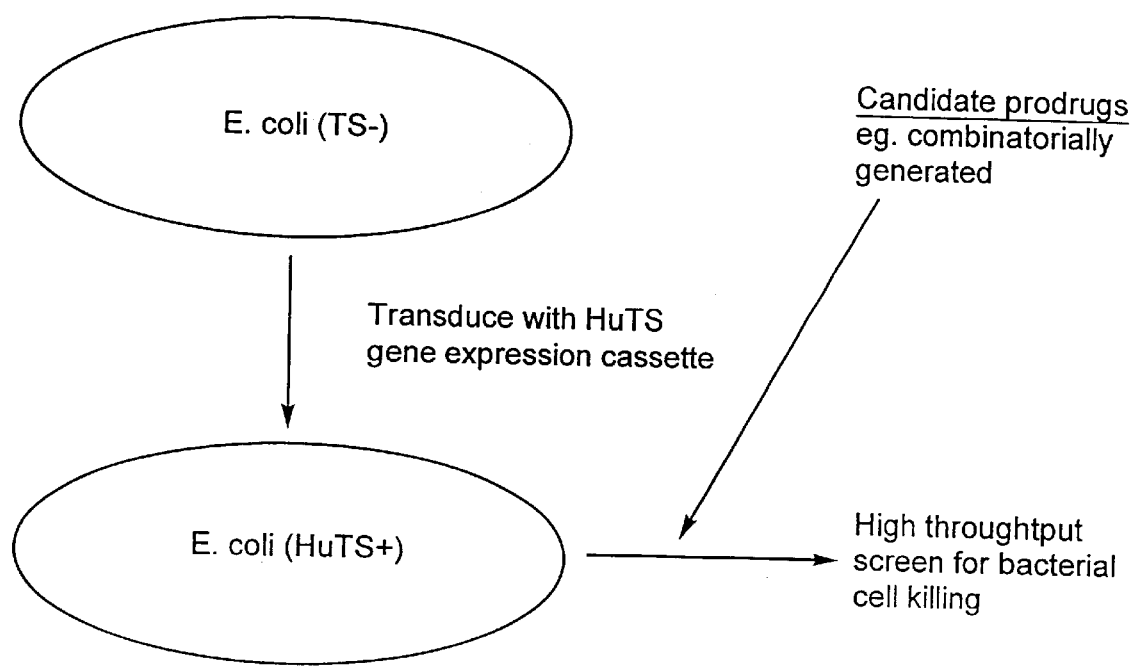
FIG. 4 schematically shows how lead human thymidylate synthase (TS) prodrugs are assayed using TS-negative *E. coli* as the cell target.

For example and as shown in FIG. 4, a foreign gene, e.g., a human gene encoding TS, can be inserted into the host cell such that human TS is expressed. This genetically engineered cell is shown as the "test cell" in FIG. 3. The "control cell" does not express the target enzyme. In some embodiments it may be necessary to supplement the culture media with the protein product of the target enzyme.

In a separate embodiment, the wild type host cell is deficient or does not express more than one enzyme of interest. As shown in FIG. 4, the host cell does not endogenously produce thymidine kinase (TK⁻) or thymidylate synthase (TS⁻). Genes coding for the human counterpart of these enzymes are introduced into the host cell to obtain the desired level of expression. The level of expression of enzyme in each transfected cell line can be monitored by methods described herein, e.g., by immunoblot and enzyme assay in cell lysates, using monoclonal or polyclonal antibody previously raised against the enzyme for immunodetection. See, e.g., as described by Chen, L. et al. (1996). Enzymatic assays also can be performed as reviewed by Carreras, C. W. and Santi, D. N. (1995) using detectably labeled substituents, e.g. tritium labeled substituents.

The test cell is grown in small multi-well plates and is used to detect the biologic activity of test prodrugs. For the purposes of this invention, the successful candidate drug will block the growth or kill the test cell type, but leave the control cell type unharmed.

The candidate prodrug can be directly added to the cell culture media or previously conjugated to a ligand specific to a cell surface receptor and then added to the media. Methods of conjugation for cell specific delivery are well known in the art, see e.g., U.S. Pat. Nos. 5,459,127; 5,264,618; and published patent specification WO 91/17424 (published Nov. 14, 1991). The leaving group of the candidate prodrug can be detectably labeled, e.g., with tritium. The target cell or the culture media is then assayed for the amount of label released from the candidate prodrug. Alternatively, cellular uptake may be enhanced by packaging the prodrug into liposomes using the method described in Lasic, D. D. (1996) or combined with cytofectins as described in Lewis, J. G. et al. (1996).

In a separate embodiment, cultured human tumor cells overexpressing the enzyme of interest i e., target enzyme, are identified as described above. The cells are contacted with the potential therapeutic agent under conditions which favor the incorporation of the agent into the intracellular compartment of the cell. The cells are then assayed for inhibition of cellular proliferation or cell killing.

Provided below is a brief summary of cells and target enzymes that are useful to activate the prodrugs of this this invention.

Thymidylate Synthase

The overexpression of thymidylate synthase is associated with colon cancer, breast cancer, gastric cancer, head and neck cancer, liver cancer and pancreatic cancer. These diseases are currently treated by antimetabolite drugs (uracil-based, folate-based, or quinaszoline-based, (see Table 1)). In each of these cases it is likely that the 5-flurouracil therapy can lead to amplified activity of TS, or select for drug resistant forms of the enzyme, and thereby lead to drug-resistance of the disease relapse. Lönn, U. et al. (1996) reported that amplification of the TS gene occurred in breast cancer patients who previously received adjuvant chemotherapy (cyclophosphamide, methotrexate, 5-fluorouracil [CMF]) after surgery. The principal reaction normally performed by TS is the synthesis of deoxythymidine monophosphate (dTMP) and dihydrofolate (DHF) from deoxyuridine monophosphate (dUMP) and N(5),N(10)-methylene-tetrahydrofolate (THF). In one embodiment, a derivative of uracil or THF is provided to cells expressing TS. For purposes of is invention, "uracil" (base only) and "uridine" (base and sugar) are used interchangeably and synonomously.

The derivative or "prodrug" is converted by the enzyme into highly cytotoxic metabolites. The low level of TS expressed in normal cells will not produce a toxic amount of the converted toxin. High levels of TS expressed in disease tissues generate more toxin and thereby lead to an inhibition of cell proliferation and/or cell death. For example, current therapy utilizes 5-fluorodeoxyuridylate to inhibit TS activity. During the reaction with substrate, the fluorine atom irreversibly binds to the TS enzyme and inhibits it. In contrast to one embodiment of the present invention, the prodrugs allow TS to complete the reaction but generates a modified product that, when incorporated into DNA, causes a toxic effect. The enzyme product may also block other critical cellular functions (e.g. protein synthesis or energy metabolism). Conversion of the prodrug also can release a metabolite, such as Br⁻ or I⁻ or CN⁻ which is toxic to the cell. Derivatives of uracil/dUMP and N(5)(10)-THF can be synthesized, all of which have the potential of generating toxic product after metabolically catalyzed by TS.

Synthesis of 5-substituted pyrimidine nucleosides and 5-substituted pyrimidine nucleoside monophosphates can be accomplished by methods that are well-known in the art. For example, treatment of 5-chloromercuri-2'-deoxyuridine with haloalkyl compounds, haloacetates or haloalkenes in the presence of $Li_2PdCl_4$ results in the formation, through an organopalladium intermediate, of the 5-alkyl, 5-acetyl or 5-alkene derivative, respectively. Wataya, et al. (1979) and Bergstrom, et al. (1981). Another example of C5-modification of pyrimidine nucleosides and nucleotides is the formation of C5-trans-styryl derivatives by treatment of unprotected nucleotide with mercuric acetate followed by addition of styrene or ring-substituted styrenes in the presence of $Li_2PdCl_4$. Bigge, et al. (1980). Pyrimidine deoxyribonucleoside triphosphates were derivatized with mercury at the 5 position of the pyrimidine ring by treatment with mercuric acetate in acetate buffer at 50° for 3 hours. Dale, et al. (1973). Such treatment would also be expected to be effective for modification of monophosphates; alternatively, a modified triphosphate could be converted enzymatically to a modified monophosphate, for example, by controlled treatment with alkaline phosphatase followed by purification of monophosphate. Other moieties, organic or nonorganic, with molecular properties similar to mercury but with preferred pharmacological properties could be substituted. For general methods for synthesis of substituted pyrimidines, for example, U.S. Pat. Nos. 4,247,544; 4,267,171; and 4,948,882; and Bergstrom et al. (1981). The above methods would also be applicable to the synthesis of derivatives of 5-substituted pyrimidine nucleosides and nucleotides containing sugars other than ribose or 2'-deoxyribose, for example 2'-3'-dideoxyribose, arabinose, furanose, lyxose, pentose, hexose, heptose, and pyranose. An example of such a substituents are halovinyl groups, e.g. E-5-(2-bromovinyl)-2'-deoxyuridylate. Barr, P. J. et al. (1983). In this reference the authors demonstrated that the normally inert substituent at the 5-position (bromovinyl) is convertible to a chemically reactive group as a result of enzyme-mediated nucleophilic attack at the 6-position of the uridine heterocycle, leading to the production of a reactive alkylating agent. This compound is not useful from the point of view of the current application because it cannot be activated by endogenous thymidine kinase, and because its conversion by thymidylate synthase leads to inactivation of the thymidylate synthase Balzarini, et al., 1987). However, improved substituents will be synthesized and compared for reactivity with TS and specific cytotoxicity to TS-overproducing tumor cells.

Alternatively, 5-bromodeoxyuridine, 5-iododeoxyuridine, and their monophosphate derivatives are available commercially from Glen Research, Sterling, Va. (USA), Sigma-Aldrich Corporation, St. Louis, Mo. (USA), Moravek Biochemicals, Inc., Brea, Calif. (USA), ICN, Costa Mesa, Calif. (USA) and New England Nuclear, Boston, Mass. (USA). Commercially-available 5-bromodeoxyuridine and 5-iododeoxyuridine can be converted to their monophosphates either chemically or enzymatically, though the action of a kinase enzyme using commercial available reagents from Glen Research, Sterling, Va. (USA) and ICN, Costa Mesa, Calif. (USA). These halogen derivatives could be combined with other substituents to create novel and more potent antimetabolites.

Primary sequences show that TS is one of the most highly conserved enzymes. Perry, K. et al. (1990). Crystal structures of TS from several procaryotic species, *Lactobacillus casei* (Hardy, L. W. et al. (1987); Finer-Moore, J. et al. (1993)) and *Escherichia coli* (Perry, K. et al. (1990)); an eukaryote *Leishmania major* (Knighton, E. R. et al. (1994)); and T4 phage (Finer-Moore, J. S. et al., (1994)) have been determined and indicate that tertiary structure also is very well conserved. The sequence alignment of the species of TS whose three dimensional structures have been determined and is shown in Schiffer, C. A. et al. (1995). From these amino acid sequences, the DNA sequences can be deduced or isolated using methods well known to those of skill in the art. Sambrook, et al. (1989). Alternatively, some 29 TS sequences from different organisms have been cloned and deposited into the DNA databases as described in Carreras, C. W. and Santi, D. V. (1995). The sequence of human thymidylate synthase gene, its cloning, expression and purification is provided in Takeishi, K. et al. (1985), Davisson, V. J. et al. (1989) and Davisson, V. J. et al. (1994). Genes encoding the TS protein and containing the necessary regulatory sequences, are constructed using methods well known to those of skill in the art. The gene encoding TS is introduced to target cells by electroporation, transformation or transfection procedures. Sambrook et al. (1989). Alternatively, the gene is inserted into an appropriate expression vector by methods well known in the art, e.g., as described in Carreras, C. W. and Santi, D. V. (1995), Miller (1992) and Spector et al. (1997). The expression vector inserts the TS gene into the cells. The cells are then grown under conditions which favor the expression and production of TS protein.

Human gastric cancer cell lines, MKN-74, MKN-45, MKN-28 and KATO-III can be used in the assay described above to identify potential therapeutic agents which are selective substrates for TS. MKN-74 and MKN-45 are established from well and poorly differentiated adenocarcinomas, respectively. These cell lines and culture conditions are described in Osaki, M. et al. (1997) and references cited therein. Alternatively, tumor cell lines such as those described by Copur, S. et al. (1995), which have been selected by 5-FU to overexpress thymidylate synthase may be used.

Quantitation of TS can be performed using enzymatic biochemical assays that are well known to those with skill in the art. To quantify the level of TS protein and TS gene expression from human tumor tissue samples, the methods as reported by Johnston, P. G. et al. (1991) and Horikoshi, T. et al. (1992) provide sensitive assays. Alternatively, the PCR method of Lönn, U. et al. (1996) is used to assay TS gene amplification and identify cells that are useful in the method of identifying therapeutic agents as described herein.

As is apparent to one skilled in the art, control cell culture systems without drug and separately with a reference drug such as the one exemplified below, also are assayed. A preferred embodiment of the prodrugs is one which preferentially kills target cells with about 2-fold and preferably about 3-fold or greater activity than normal cells. This invention also provides the agents identified by the methods described herein.

In another aspect, this invention provides a method for inhibiting the proliferation of a hyperproliferative cell, by first conducting the above assay. A prodrug identified by this assay is contacted with the cell and converted to a toxic metabolite in the cell by an endogenous intracellular enzyme as described above.

In one embodiment, the endogenous, intracellular enzyme is thymidylate synthase and the cell is selected from the group consisting of colorectal cell, head and neck cancer cell, breast cancer cell, or a gastric cancer cell.

In a further aspect, the prodrug contacted with the cell overexpressing thymidylate synthase is an L- or D-compound of the formulae:

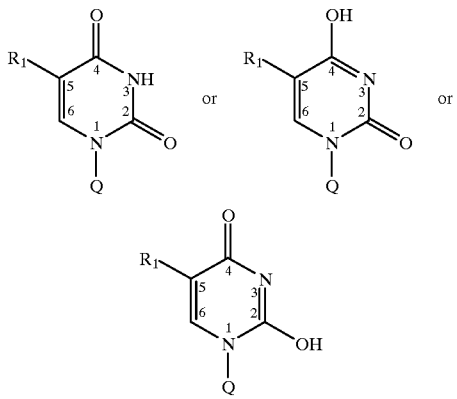

which may be in any of their enantiomeric, diasteriomeric, or stereoisomeric forms, including, for example, D- or L-forms, and for example, α- or β-anomeric forms.

In the above formulae, $R_1$ (at the 5-position) is or contains a leaving group which is a chemical entity that has a molecular dimension and electrophilicity compatible with extraction from the pyrimidine ring by thymidylate synthase, and which upon release from the pyrimidine ring by thymidylate synthase, has the ability to inhibit the proliferation of the cell or kill the cell.

In one embodiment, $R_1$ is or contains a chemical entity selected from the group consisting of: —Br, —I, —O-alkyl, —O-aryl, O-heteroaryl, —S-alkyl, —S-aryl, —S-heteroaryl, —CN, —OCN, —SCN, —NH$_2$, —NH-allyl, —N(alkyl)$_2$, —NHCHO, —NHOH, —NHO-alkyl, NH$_2$CONHO—, NHNH$_2$, and —N$_3$. Another example of $R_1$ is derived from cis-platin:

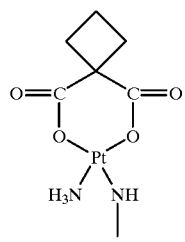

In the above formulae for the L- or D-compound(s), Q is a chemical entity selected from the group consisting of sugar groups, thio-sugar groups, carbocyclic groups, and derivatives thereof. Examples of sugar groups include, but are not limited to, monosaccharide cyclic sugar groups such as those derived from oxetanes (4-membered ring sugars), furanoses (5-membered ring sugars), and pyranoses (6-membered ring sugars). Examples of furanoses include threo-furanosyl (from threose, a four-carbon sugar); erythro-furanosyl (from erythrose, a four-carbon sugar); ribo-furanosyl (from ribose, a five-carbon sugar); ara-furanosyl (also often referred to as arabino-furanosyl; from arabinose, a five-carbon sugar); xylo-furanosyl (from xyloge, a five-carbon sugar); and lyxo-furanosyl (from lyxose, a five-carbon sugar). Examples of sugar group derivatives include "deoxy", "keto", and "dehydro" derivatives as well as substituted derivatives. Examples of thio sugar groups include the sulfur analogs of the above sugar groups, in which the ring oxygen has been replaced with a sulfur atom. Examples of carbocyclic groups include $C_4$ carbocyclic groups, $C_5$ carbocyclic groups, and $C_6$ carbocyclic groups which may further have one or more substituents, such as —OH groups.

In one embodiment, Q is a furanosyl group of the formula:

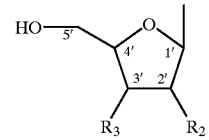

wherein $R_2$ and $R_3$ are the same or different and are independently H or —OH. In one embodiment, $R_2$ and $R_3$ are H. In one embodiment, $R_2$ is OH and $R_3$ is H. In one embodiment, $R_2$ is H and $R_3$ is OH. In one embodiment, wherein $R_2$ and $R_3$ are OH.

In one embodiment, Q is a β-D-ribofuranosyl group of the formula:

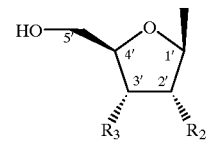

wherein $R_2$ and $R_3$ are the same or different and are independently H or —OH.

In some embodiments, the hydroxymethyl group (for example, the 4'-hydroxymethyl group of β-D-ribofuranosyl) can be phosphorylated.

Modifications of current alkylating agents attached at the pyrimidine 5-position, and which fit the steric restrictions as described above can be employed (Haskell, C. M. eds. (1995), pp. 55–58). Cell-free, or cell based, screening assays for release of constituent at the 5-position of uracil are described by Roberts, D. (1966) and Hashimoto, Y. et al. (1987).

In the case where $R_1$ comprises CN$^-$, the highly toxic CN$^-$ moiety is the therapeutically active species. Because of the highly nonspecific toxic nature of CN$^-$, it cannot normally be used in a therapeutic mode. This problem is overcome by delivering the toxin in the form of a prodrug that will be significantly activated only in cells which overexpress thymidylate synthase.

In addition, a prodrug can be converted to a toxic metabolite by the intracellular enzyme which, in some embodiments, can be further modified by an intracellular "housekeeping" enzyme. An example is shown below.

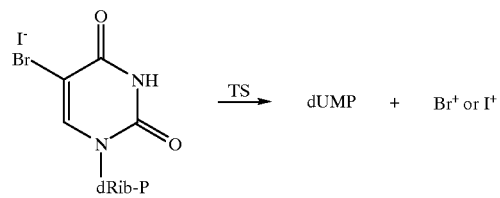

Description of the "partial" reaction of dUMP and TS, as well as relevant assays are described in Garrett, C. et al.

(1979). Assays for other products, i.e. where a reaction complete product is an anti-metabolite of the bromovinyl-derivatives of dUMP, are described by Barr, P. J., et al. (1983). Salts of the prodrugs of the present invention may be derived from inorganic or organic acids and bases. Examples of acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, can be employed in the preparation of salts useful as intermediates in obtaining the compounds of the invention and their pharmaceutically acceptable acid addition salts. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate, propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound.

Esters of the prodrugs or compounds identified by the method of this invention include carboxylic acid esters (i.e., —O—C(=O)R) obtained by esterification of the 2'-, 3'- and/or 5'-hydroxy groups, in which R is selected from (1) straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkylsulfonyl (for example, methanesulfonyl) or aralkylsulfonyl; (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di-($C_{6-24}$)acyl glycerol. In such esters, unless otherwise specified, any alkyl moiety present advantageously-contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Examples of lyxo-furanosyl prodrug derivatives of the present invention include, for example, those with chemically protected hydroxyl groups (e.g., with O-acetyl groups), such as 2'-O-acetyl-lyxo-furanosyl; 3'-O-acetyl-lyxo-furanosyl; 5'-O-acetyl-lyxo-furanosyl; 2',3'-di-O-acetyl-lyxo-furanosyl and 2',3',5'-tri-O-acetyl-lyxo-furanosyl.

Ethers of the compounds of the present invention include methyl, ethyl, propyl, butyl, isobutyl, and sec-butyl ethers.

In a further embodiment, the substrate may not be chemically related to pyrimidines or folates, but rather synthesized based upon known parameters of rational drug design. See Dunn, W. J. et al. (1996).

As is apparent to one skilled in the art control cell culture systems without drug and separately with a reference drug such as the one exemplified below, also are assayed. Compounds which preferentially kill target cells with about 2-fold and preferably 3-fold or greater activity than normal cells are preferred. This invention also provides the agents identified by the methods described herein.

Tyrosine Kinases

The tyrosine kinase superfamily comprises the EGF receptor (EGFR), the macrophage colony-stimulating factor (CSF-1) receptor (v-fins), and the insulin receptor, which shows 30 to 40% identity with the product of the ros oncogene. More specifically, the members of this superfamily include v-src, c-src, EGFR, HER2, CSF-1 receptor, c-fms, v-ros, insulin receptor, and c-mos. See FIG. 8.5 of Burck, K. B. et al., eds. (1988). Overexpression of members of the type 1 receptor tyrosine kinase superfamily has been documented in many types of cancer (Eccles, S. A. et al. (1994–95)). Overexpression of tyrosine kinases is linked to exposure to the α-cancer biologic agent TNF-α (Hudziak, R. M. et al. (1988) and Hudziak, R. M. et al. (1990)) and to chemotherapy (Stühlinger et al. (1994)).

The transforming gene of the Rous sarcoma virus, v-src, encodes an enzyme that phosphorylates, tyrosine residues on proteins. The c-src proto-oncogene is found on chromosome 20. Tissues and cell lines derived from tumors of neuroectodermal origin having a neural phenotype express high levels of c-src accompanied by high specific kinase activity.

Several groups of investigators have reported overexpression of c-erbB-2/neu ("HER2") oncogene in cancer cells. Brison (1993) noted that erbB proto-oncogene is amplified in human tumors with resultant overexpression in most cases. Amplification of the c-erbB-2/neu oncogene has been reported in human mammary tumors (Slamon, et al. (1987), van de Vijver et al. (1987), Pupa et al. (1993), and Andersen et al. (1995)) and in bladder tumors (Sauter et al. (1993)), and in every case amplification was accompanied by overexpression. c-erbB-2/neu overexpression also has been reported in ovarian cancer tissue samples (Slamon, et al. (1989), Meden et al. (1994), and Felip et al. (1995)), and tumors derived from the peripheral nervous system. Sukumar and Barbacid, (1990).

To perform the drug screening assay, tumor cell lines will be assayed for expression of the oncogene or will be engineered to express varying levels of tyrosine kinase. Selected cell lines are cultured and candidate drugs are added in varying concentrations. The cells are assayed for cell killing or inhibition of cellular proliferation, as described in Hudziak, R. M. et al. (1988) and Hudziak, R. M. et al. (1990).

Dihydrofolate Reductase

Methotrexate is a potent inhibitor of dihydrofolate reductase, an enzyme necessary for intracellular folate metabolism. Dihydrofolate reductase functions to regenerate tetrahyydrofolate from dihydrofolate, a product of the thymidylate synthase reaction (Voet, et al. eds. (1995), p. 813). It is well established that an important mechanism of resistance of cells to methotrexate is an increase in DHFR activity due to amplification of the DHFR gene. Banerjee, D. et al. (1995), Schimke, R. T. et al. (1988). Lönn, U. et al. (1996) reported that amplification of the DHFR gene occurred in breast cancer patients who previously received adjuvant chemotherapy (cyclophosphamide, methotrexate, 5-fluorouracil [CMF]) after surgery. Lack of the retinoblastoma (Rb) may also lead to enhanced MTX resistance as a consequence of an increase in DHFR mRNA expression activity without gene amplification. Li, W. W. et al. (1995). Cell lines with mutated p53 have been shown to undergo gene amplification, and the resistant cells are selected by chemotherapy. Banerjee, D. et al. (1995), Yin, Y. et al. (1992) and Livingston, L. R. et al. (1992). For the purposes of performing the assay of this invention, Schimke, R. T. et al. (1988) describes several mouse, hamster and human cell lines. Alternatively, the PCR method of Lönn U. et al. (1996) is used to assay DHFR gene amplification and identify cells that are useful in the method of identifying therapeutic agents as described herein. The nucleotide sequence of the cDNA coding for the human dihydrofolate reductase is provided in Masters, J. N. and Attardi, G. (1983) and cells can be engineered to express varying levels of the enzyme as noted herein. Dicken, A. P. et al. (1993) describes a mutant DHFR gene selected by chemotherapy. Purification of DHFR and assays related to enzyme function are described in Nakano, T. et al. (1994). Alternatively, cDNA encoding DHFR is transfected into NIH 3T3 cells. Candidate drugs are added in varying concentrations and cell killing and inhibition of proliferation are assayed.

Antimetabolites dependent on dihydrofolate reductase activity can be synthesized by the attachment of, for example, an alkylating group to either the N5 or the C6 position of dihydrofolate. Reduction of the N5-C6 bond by DHFR will result in the release of the alkylating agent. In addition to the alkylating groups, any moiety whose release by DHFR results in the production of a toxin or an antimetabolite will be useful in the practice of the invention.

Multidrug Resistant Tumors

Multidrug resistance (MDR) is a generic term for the variety of strategies tumor cells use to evade the cytotoxic effects of anticancer drugs. MDR is characterized by a decreased sensitivity of tumor cells not only to the drug employed for chemotherapy but also to a broad spectrum of drugs with neither obvious structural homology nor common targets. This pleiotropic resistance is one of the major obstacles to the successful treatment of tumors. MDR may result from structural or functional changes at the plasma membrane or within the cytoplasm, cellular compartments, or nucleus. Molecular mechanisms of MDR are discussed in terms of modifications in detoxification and DNA repair pathways, changes in cellular sites of drug sequestration, decreases in drug-target affinity, synthesis of specific drug inhibitors within cells, altered or inappropriate targeting of proteins, and accelerated removal or secretion of drugs.

One of the mechanisms implicated in MDR results from amplification and over-expression of a gene known as the ATP-dependent multidrug resistant associated protein (MRP) in drug selected cell lines. For a review of the mechanisms of MDR, see Gottesman, M. M. et al. (1995) and Noder et al. (1996).

To establish MDR cell lines, drug selections are conducted in either a single step or in multiple steps as described in Gottesman, M. M. et al. (1995) and Simon, S. M. and Schindler, M. (1994), and references cited therein. The isolation of DNA sequences coding for MDR from various mammalian species is described in Gros, P. et al. (1986), Gudkov, A. V. et al. (1987), and Roninson, I. B. et al. (1984), and reviewed in Gottesman, M. M. et al. (1995), and cells can be engineered to express varying levels of this enzyme as described above. The prodrug targeting MDR will be based upon the ATPase activity of this transporter.

Ribonucleotide Reductase

The ribonucleotide reductase reduces ribonucleoside diphosphates to the corresponding deoxyribonucleoside diphosphates. The enzyme is a tetramer made up of two α-subunits and two β-subunits. Hydroxyurea specifically blocks this reaction by interacting with the tyrosyl free radical (Tyr-122) of the $\beta_2$-substrate complex. Voet et al. (1995). The goal in targeting this reaction is to allow the accumulation of the free radical product $O_2^-$, which is highly cytotoxic.

Application of Technology to Other Diseases

While the primary focus of this application is directed to cancer, it should be recognized that the technology is broadly applicable to other diseases, especially antibiotic resistant bacterial infections. The β-lactam antibiotics encounter resistance in bacteria as the result of overexpression of β-lactamases. Hamilton-Miller, J. M. T. and Smith, J. T. eds. (1979) p. 443. Other enzymes, such as the aminoglycoside phosphotransferese Type III, are induced and selected for following treatment with aminoglycoside antibiotics, such as kanamycin. McKay, G. A. et al. (1994). For the purpose of this application, prodrug substrates derived from known substrates will be prepared that will not block enzyme activity, but will instead take advantage of the high enzyme activity to generate intracellular toxins in the infectious agents.

In Vivo Administration

The in vitro assays are confined in animal models bearing human tumors or infected with an antibiotic resistant microorganism to determine in vivo efficacy.

Another aspect of this invention is a method for treating a pathology characterized by hyperproliferative cells in a subject comprising administering to the subject a therapeutic amount of a prodrug that is converted to a toxin in a hyperproliferative cell by an endogenous intracellular enzyme as defined herein.

When the prodrug is administered to a subject such as a mouse, a rat or a human patient, the agent can be added to a pharmaceutically acceptable carrier and systemically or topically administered to the subject. To determine patients that can be beneficially treated, a tumor sample is removed from the patient and the cells are assayed for the level of expression of the enzyme of interest. If the expression is above that expressed in normal cells and an amount of the prodrug effective to kill or inhibit the cell can be administered without undesirable side effects, then the prodrug is a preferred embodiment. Therapeutic amounts can be empirically determined and will vary with the pathology being treated, the subject being treated and the toxicity of the converted prodrug or cellular toxin. When delivered to an animal, the method is useful to further confirm efficacy of the prodrug. As an example of an animal model, groups of nude mice (Balb/c NCR nu/nu female, Simonsen, Gilroy, Calif.) are each subcutaneously inoculated with about $10^5$ to about $10^9$ hyperproliferative, cancer or target cells as defined herein. When the tumor is established, the prodrug is administered, for example, by subcutaneous injection around the tumor. Tumor measurements to determine reduction of tumor size are made in two dimensions using venier calipers twice a week. Other animal models may also be employed as appropriate. Lovejoy, et al. (1997) and Clarke, R. (1996).

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The agents and compositions of the present invention can be used in the manufacture of medicaments and for the treatment of humans and other animals by administration in accordance with conventional procedures, such as an active ingredient in pharmaceutical compositions.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to a compound of the present invention, the pharmaceutical compositions can also contain other pharmaceutic ally active compounds or a plurality of compounds of the invention.

More particularly, a compound of the formula of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, and the disease being treated.

In general, a suitable dose for each of the above-named compounds, is in the range of about 1 to about 100 mg per kilogram body weight of the recipient per day, preferably in the range of about 1 to about 50 mg per kilogram body weight per day and most preferably in the range of about 1 to about 25 mg per kilogram body weight per day. Unless otherwise indicated, all weights of active ingredient are calculated as the parent compound of the formula of the present invention for salts or esters thereof, the weights would be increased proportionately. The desired dose is preferably presented as two, three, four, five, six or more sub-doses administered at appropriate intervals throughout the day. These sub-doses may be administered in unit dosage forms, for example, containing about 1 to about 100 mg, preferably about 1 to above about 25 mg, and most preferably about 5 to above about 25 mg of active ingredient per unit dosage form. It will be appreciated that appropriate dosages of the compounds and compositions of the invention may depend on the type and severity and stage of the disease and can vary from patient to patient. Determining the optimal dosage will generally involve the balancing of the level of therapeutic benefit against any risk or deleterious side effects of the treatments of the present invention.

Ideally, the prodrug should be administered to achieve peak concentrations of the active compound at sites of disease. This may be achieved, for example, by the intravenous injection of the prodrug, optionally in saline, or orally administered, for example, as a tablet, capsule or syrup containing the active ingredient. Desirable blood levels of the prodrug may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

While it is possible for the prodrug ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For diseases of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the prodrug may be employed with either a paraffinic or a water-miscible ointment base. Alternatively, the prodrug ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof The topical formulations may desirably include a compound which enhances absorption or penetration of the prodrug ingredient through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the prodrug ingredient. The prodrug ingredient is preferably present in such formulation in a concentration of about 0.5 to about 20%, advantageously about 0.5 to about 10% particularly about 1.5% w/w.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the prodrug ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the prodrug ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of a prodrug ingredient.

It should be understood that in addition to the ingredients particularly mentioned above, the formulations of this invention may include other agents conventional in the art having regard to the type of formulation in question, for example, those suitable of oral administration may include such further agents as sweeteners, thickeners and flavoring agents.

Prodrugs and compositions of the formula of the present invention may also be presented for the use in the form of veterinary formulations, which may be prepared, for example, by methods that are conventional in the art.

EXAMPLES

The following examples are specifically directed to the target enzyme TS. It is apparent to those skilled in the art that the following methods can be modified for the discovery of other prodrugs to target enzymes as defined herein.

Chemical and Cell-based Assays

Pyrimidine-based prodrugs are chosen based on the ability to react with intracellular thymidylate synthase, and release the toxin into the medium without inactivating the enzyme. Candidate drugs are screened in reaction mixtures containing human thymidylate synthase with and without N5N10-methylenetetrahydrofolate, and the candidate prodrug. The leaving group of the candidate prodrug (e.g., at the pyrimidine 5 position) is labeled, for example, with tritium using methods well known in the art. The control substrate is similarly labeled (e.g. $5\text{-}^3\text{H}$) dUMP, under the same reaction conditions. The assays are done similarly to the description provided in Carreras, C. W. and Santi, D. V. (1995), and references cited therein. The human thymidine synthase can be purified from E. coli containing the expressed human thymidylate synthase. See Davisson, V. J. et al. (1989) and Davisson, V. J. et al. (1994). This approach provides a scaleable assay capable of screening large numbers of candidate compounds.

Figure 5:
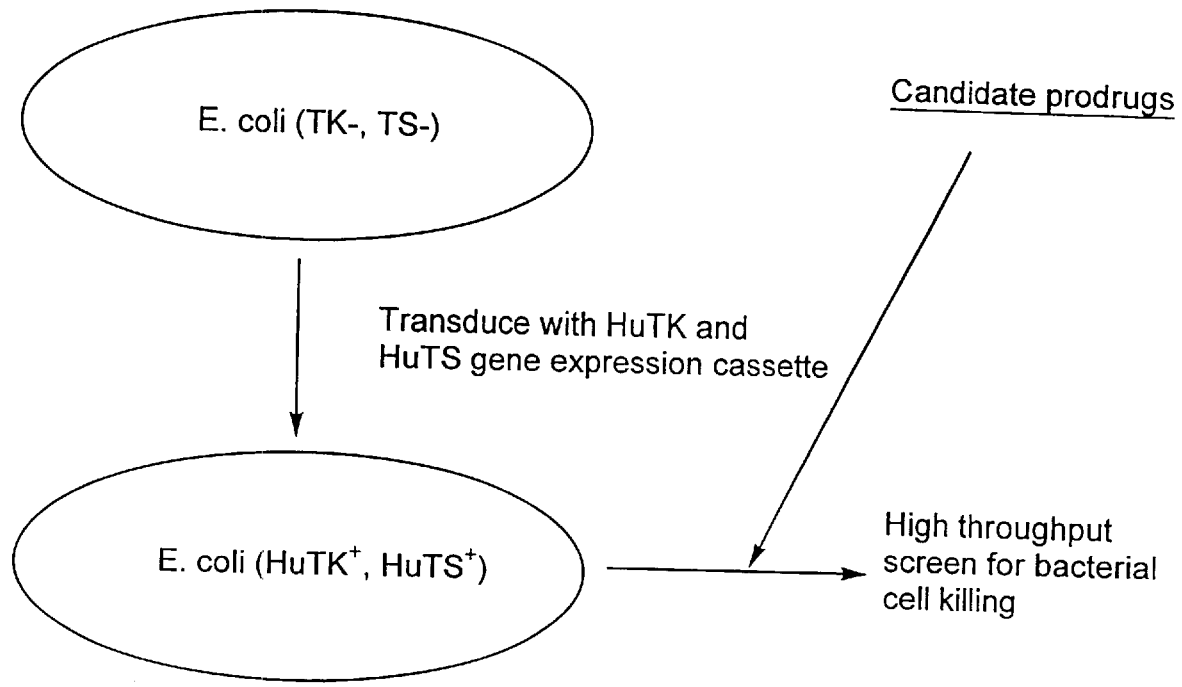
FIG. 5 shows an example of how to use this screen to simultaneously optimize the prodrug for reactivity to two target enzymes.

A high throughput screen to identify biologically active compounds is outlined in FIGS. 3, 4 and 5. The basis of the test is the ease of genetic manipulation and growth of E. coli, and similar single cell organisms (e.g. yeast), see Miller (1992) and Spector, et al. (1997). The key step is removing the endogenous enzyme activity corresponding to an enzyme target for prodrug design. This can be done by any of the methods described by Miller (1992), Sambrook (1989) or Spector et al. (1997). These methods include chemical and biologic (e.g. viral or transponson insertional) mutagnesis, followed by an appropriate selection procedure. The TS negative (TS⁻) cell then becomes a negative control for the identification of prodrugs that, when acted upon by thymidylate synthase, become cell toxins. A similar approach can be made with other cell types, e.g. other bacteria, yeast, or other selectable single cell organisms. In the assay, both control and recombinant organisms are compared for sensitivity to the test compounds. As will be understood by those skilled in the art, prodrugs which distinguish between species of enzyme can also be derived from this procedure. For example, otherwise identical cells expressing human and yeast enzymes can be used to detect antibiotic prodrugs which are preferentially toxic only to the cells expressing the yeast enzyme. In this way, novel and specific antibiotics can be discovered.

Example cell lines are ras-transformed NIH 3T3 cells (obtained from the ATCC) and are engineered to express increasing quantities of human thymidylate synthase (Hu TS) from the cloned cDNA. Transfection is done in a transient or permanent basis (see Chen, L. et al. (1996), Hudziak, R. M. et al. (1988), and Carter, P. et al. (1992). NIH-000 (ras-transformed parent cell line); NIH-001 (low expresser of HuTS); NIH-002 (intermediate expressor of Hu TS); NIH-003 (high expresser of HuTS). The level of expression of TS in each cell line is monitored by immunoblot and enzyme assay in cell lysates, using antibody directed versus HuTS protein for immunodetection (e.g., as described in Chen, L. et al. (1996)). Enzymatic assays are performed as reviewed by Carreras, C. W. and Santi, D. N. (1995).

Human colorectal and breast tumor cell lines are screened for expression of HuTS enzyme. Cell lines expressing low, moderate and high levels of HuTS will be exposed to drug candidates as described above for the NIH 3T3 cell lines. Growth inhibition and cytotoxicity are monitored as described above. Similar tests can be carried out for each of the enzymes listed in Table 1.

In Vivo Testing

Ras-transformed NIH 3T3 cell lines are transplanted subcutaneously into immunodeficient mice. Initial therapy may be direct intratumoral injection. The expected result is that increased level of expression of HuTS or a target enzyme leads to enhanced antitumor activity by the drug candidates. Similar studies are performed with human tumors expressing increasing levels of HuTS or a target enzyme, and demonstrating that efficacy in response to drug correlates with their level of HuTS expression or target enzyme. Optionally, experiments are be performed as above except the drug will be administered intravenously into the animals to address issues related to efficacy, toxicity and pharmacobiology of the drug candidates.

The in vivo studies will be conducted as described by Harris, M P et al. (1996) and Antelman, D. et al. (1995).

While the invention has been described in detail herein and with reference to specific embodiments thereof, it will be apparent to one skilled in the art that various changes and modifications can be made to the invention as described above without departing from the spirit and scope thereof.

REFERENCES

Literature

Akdas, A. et al. (1996) Eur. Urol. 29(4):483–486
Almasan, A. et al. (1995) Cancer Metastases Rev. 14:59–73
Andersen, et al. (1995) Acta Oncol 34(4):499–504
Antelman, D. et al., (1995) Oncogene 10:697
Balzarini, J. et al. (1987) Molecular Pharm. 32:410–16
Banerjee, D. et al. (1995) Acta Biochem. Pol. 42(4):457–464
Barbour, K. W. et al. (1992) Mol. Pharmacol. 42:242–8
Barr, P. J. et al. (1983) J. Biol. Chem. 258(22):13627–31
Bergstrom, et al. (1981) J. Org. Chem. 46:1432–1441
Bertino, J. R. et al. (1996) Stem Cells 14:5–9
Bigge, et al (1980) J. Amer. Chem. Soc. 102:2033–2038
Brison (1993) Biochem. Biophys. Acta 1155(1):25–41
Budavari, eds., Merck Index (12$^{th}$ Ed., 1996)
Burck, K. B. et al. eds. "Oncogenes: An Introduction to the Concept of Cancer Genes" (Springer-Verlag, New York 1988)
Callahan, A. P., et al. (1989) Commun Nucl Med 20: 3–6
Carreras, C. W. and Santi, D. V. (1995) Annu. Rev. Biochem 64:721–762
Carter, P. et al. (1992) Proc. Natl. Acad. Sci. USA 89:4285–4289
Chen, L. et al. (1996) Cancer Research 56:1331–1340
Clarke, R. (1996) Brest Cancer Res. Treat. 39:1–6
Connors, T. A. (1986) Xenobiotica 16(10/11):975–988
Connors, T. A. and Knox, R. J. (1995) Stem Cells 13:501–511
Connors, T. A. (1996) Ann. Oncol. 7:445
Copur, S. et al. (1995) Biochem. Pharm. 49(10):1419–26
Dale, et al. (1973) Proc. Natl. Acad. Sci. USA 70:2238–2242
Davisson, V. J. et al. (1989) J. Biol. Chem. 264:9145–48
Davisson, V. J. et al. (1994) J. Biol. Chem. 269:30740
Dicken, A. P. et al. (1993) Proc. Natl. Acad. Sci. USA 90:11797–801
Dorr, R. T. and Von Hoff, D. D., eds. "Cancer Chemotherapy Handbook" 2nd ed. (Appleton and Lange 1994), pp. 768–773, 1020
Dunn, W. J. et al. (:1996) J. Med. Chem., 39:4825
Eccles, S. A. et al. (1994–95) Invasion Metast. 14(1–6):337–348
Felip, et al. (1995) Cancer 75(8):2147–2152
Finer-Moore, J. et al. (1993) J. Mol. Bio. 232:1101–116
Finer-Moore, J. S. et al. (1994) Biochemistry 33:15459–15468
Fries, K. M., et al. (1995) J. Med Chem 38:2672–80
Garrett, C. et al. (1979) Biochem 18:2798–2804
Gottesmanm, M. M. et al. (1995) Annu. Rev. Genet. 29:607–649
Gros, P. et al. (1986) Nature 323:728–731
Gros, P. et al. (1986) Cell 47:371–80
Gros, P. et al. (1986) Proc. Natl. Acad. Sci. USA 83:337–41
Gudkov, A. V. et al. (1987) Somat. Cell Mol. Genet. 13:609–19
Hamilton-Miller, J. M. T. and Smith, J. T., eds. B-Lactamases (Academic Press, 1979)
Hardy, L. W. et al. (1987) Science 235:448–455
Harris, M. P. et al. (1996) Cancer Gene Therapy 3:121
Hashimoto, Y. et al.. (1987) Anal. Biochem. 167:340–346
Haskell, C. M. ed. Cancer Treatment 4th Ed., J. Dyson, Ed., (Philadelphia: W.B. Saunders Co. 1995)
Hengstschlager, M. et al. (1996) Oncogene 12:1635–43
Horikoshi, T. et al. (1992) Cancer Res. 52:108–116
Houze, T. A. (1997) Tumour Biol. 18:53–68
Hudziak, R. M. et al. (1988) PNAS USA 85:5102–5106
Hudziak, R. M. et al. (1990) Cell Growth & Differentiation 1:128–134
Jackman, A. L. et al. (1995) Anti-cancer Drug Design 10:573–589
Johnson, P. G. et al. (1997) J. Clin. Oncol. 15:1923–1931
Johnston, P. G. et al. (1991) Cancer Res. 51:6668–6676

Kashani-Sabet, et al. (1988) *Cancer Res* 48:5775–5778
Knighton, E. R. et al. (1994) *Nature Struct. Biol.* 1:186–194
Kobayashi, H. et al. (1995) *Japanese J. Cancer Res.* 86:1014–1018
Lam, K. S. (1997) *Anticancer Drug Research* 12:145–67
Lasic, D. D. (1996) *Nature* 380:561–2
Lewis, J. G. et al. (1996) *Proc. Natl. Acad. Sci.* 93:3176–81
Li, W. W. et al. (1995) *Proc. Natl. Acad. Sci. USA* 92,10436–40
Lin W-Y., et al. (1997) *Eur J. Nucl. Med* 24: 590–595
Livingstone, L. R. et al. (1992) *Cell* 70:923–936
Lönn, U. et al. (1996) *Cancer* 77(1):107–112
Lovejoy, et al. (1997) *J. Pathol.* 181:130–5
Masters, J. N. and Attardi, G. (1983) *Gene* 21:59–63
McGuigan, C. et al. (1984) *FEBS Let* 35:11–14
McKay, G. A. et al. (1994) *Biochem* 33:6936–6944
Meden, et al. (1994) *J. Cancer Res. Clin. Oncol.* 120(6):378–81
Melton, R. G. and Sherwood, R. E. (1996) *J. Natl. Cancer Inst.* 88:153–65
Miller, J. H. "A short course in bacterial genetics: A laboratory manual and handbook for *E. coli* and related bacteria" (Cold Spring Harbor Press 1992)
Morgan, A. S. et al. (1998) *Cancer Res.* 58:2568–2575
Nakano, T. et al. (1994) *Biochemistry* 33:9945–52
Noder, et al. (1996) *Pathol. Res. Pract.* 192:768–80
Osaki, M. et al. (1997) *Apoptosis* 2:221–226
Perry, K. et al. (1990) *Proteins* 8:315–333
Peters, G. J. et al. (1995) *Eur. J. Cancer* 31A:1299–1305
Pupa, et al. (1993) *Oncogene* 8(11):2917–23
Roberts, D. (1966) *Biochem.* 5:3546–3548
Roninson, I. B. et al. (1984) *Nature* 309:626–28
Sambrook, et al., eds. "Molecular Biology: A Laboratory Manual" ($2^{nd}$ ed.) (Cold Spring Harbor Press 1989)
Sauter, et al. (1993) *Cancer Res.* 53(10 Suppl.):2199–203
Schaechter, M. et al., eds. "Mechanisms of Microbial Disease" ($2^{nd}$ ed.) (Williams and Wilkins 1993)
Schiffer, C. A. et al. (1995) *Biochemistry* 34:16279–16287
Schimke, R. T. et al. (1988) *J. Biol. Chem.* 263:5989–5992
Segovia, M. (1994:) *Ann. Tropical Med. Paras.* 88(2):123–130
Shepard, H. M. et al. (1988) *J. Clin. Immunol.* 8:353–395
Simon, S. M. and Schindler, M. (1994) *PNAS USA* 91:3497–3504
Slamon, D. J. et al. (1987) *Science* 235:177–182
Slamon, D. J. et al. (1989) *Science* 244:707–712
Simon, S. M. and Schindler, M. (1994) *Proc. Natl. Acad. Sci.* 91(9):3497–3504
Smith, K. A. et al. (1995) *Philos Tran Royal Soc* 347:49–56
Snydman, D. R. et al. (1996) *Clinical Infectious Diseases* 23(Suppl. 1):554–65
Spector, D. L. et al. "Cells, A laboratory manual" (1997)
Stühlinger, M. et al. (1994) *J. Steroid Biochem. Molec. Biol.* 49(1):39–42
Sukumar and Barbacid (1990) *Proc. Natl. Acad. Sci. USA* 87(2):718–722
Takeishi, K. et al. (1989) *Nucl. Acid Res.* 13:2035–2043
Tannock, I. F. (1996) *J. Clin. Oncol.* 14(12):3156–3174
Troutner, D. A. (1987) *Nucl Med Biol* 14: 171–176
van de Vijver, et al. (1987) *Mol. Cell. Biol.* 7(5):2019–23
Voet, et al. eds. *Biochemistry* 2nd Ed. (John Wiley & Sons, Inc. 1995)
Wataya, et al. (1979) *J. Med. Chem.* 22:339–340
Wettergren, Y. et al. (1994) *Mol. Genet.* 20:267–85
Wilson, J. D., et al. (eds.) "Harrison's Principles of Internal Medicine" ($12^{th}$ ed) (McGraw-Hill, Inc. 1991) 2208, esp. 21–76
Yin, Y et al. (1992) *Cell* 70:937–948
Yin, Y. et al. (1994) *Cancer Res.* 54:3686–91

PATENT DOCUMENTS

U.S. Pat. No. 4,247,544, Bergstrom, D. E. et al. "C-5 Substituted Uracil Nucleosides", issued Jan. 27, 1981
U.S. Pat. No. 4,267,171, Bergstrom, D. E. et al. "C-5 Substituted Cytosine Nucleosides" issued May 12, 1981
U.S. Pat. No. 4,948,882, Ruth, J. L. "Single-Stranded Labelled Oligonucleotides, Reactive Monomers and Methods of Synthesis" issued Aug. 14, 1990
U.S. Pat. No. 4,975,278, Senter, P. D. et al. "Anti-body-Enzyme Conjugates in Combination with Prodrugs for the Delivery of Cytotoxic Agents to Tumor Cells" issued Dec. 4, 1990
U.S. Pat. No. 5,085,983, Scanlon, K. J. "Detection of human tumor progression and drug resistance" issued Feb. 4, 1992
U.S. Pat. No. 5,233,031, Borch, R. F. et al. "Phosphoramidate Analogs of 2'-Deoxyuridine" issued Aug. 3, 1993
U.S. Pat. No. 5,264,618, Felgner, P. L. et al. "Cationic Lipids for Intracellular Delivery of Biologically Active Molecules" issued Nov. 23, 1993
U.S. Pat. No. 5,459,127, Felgner, P. L. et al. "Cationic Lipids for Intracellular Delivery of Biologically Active Molecules" issued Oct. 17, 1995
U.S. Pat. No. 5,627,165, Glazier, A. "Phosphorous Prodrugs and Therapeutic Delivery Systems Using Same" issued May 6, 1997
PCT Application WO 91/17474, published Nov. 4, 1991.

What is claimed is:

1. A method for inhibiting the proliferation of a hyperproliferative cell, comprising contacting the cell with a prodrug that is selectively converted to a toxin in the cell by endogenous, intracellular thymidylate synthase, wherein the prodrug is an L- or D-compound of the formula:

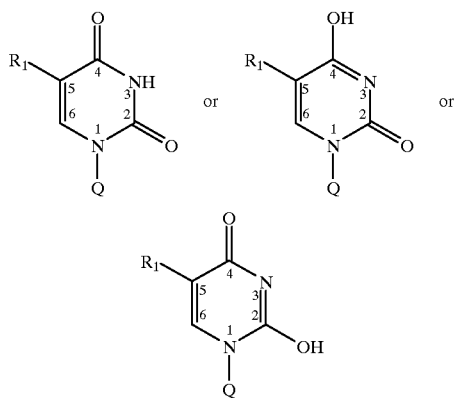

wherein $R_1$ is a toxic metabolite extractable from the pyrimidine ring by thymidylate synthase and wherein $R_1$ is selected from the group consisting of —Br, —I, —O-alkyl, —O-aryl, O-heteroaryl, —S-alkyl, —S-aryl, —S-heteroaryl, —CN, —OCN, —SCN, —NH$_2$, —NH-alkyl, —N(alkyl)$_2$, —NHCHO, —NHOH, —NHO-alkyl, NH$_2$CONHO—, NHNH$_2$, and —N$_3$; and wherein Q is selected from the group consisting of sugar groups, thio-sugar groups, carbocyclic groups and salts thereof.

2. The method of claim 1, wherein the hyperproliferative cell is characterized by the endogenous overexpression of intracellular thymidylate synthase.

3. The method of claim 1, wherein Q is a furanosyl group of the formula:

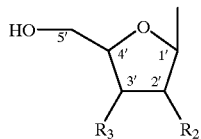

wherein $R_2$ and $R_3$ are the same or different and are independently H or —OH.

4. The method of claim 1, wherein Q is a θ-D-ribofuranosyl group of the formula:

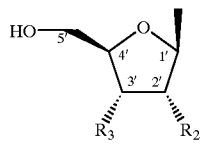

wherein $R_2$ and $R_3$ are the same or different and are independently H— or —OH.

5. A method for treating a pathology characterized by neoplastic hyperproliferative cells in a subject comprising administering to the subject a prodrug that is converted to a toxin in a neoplastic hyperproliferative cell by intracellular thymidylate synthase that is endogenously overexpressed or over-accumulated in the cell; wherein the prodrug is an L- or D-compound of the formula:

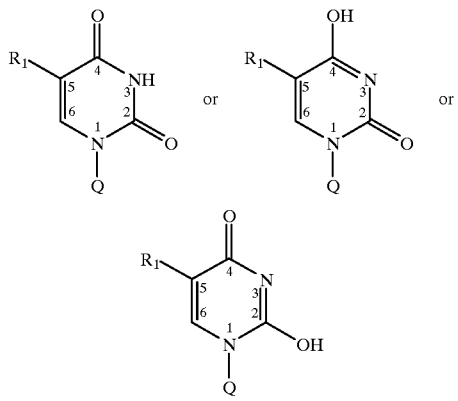

wherein $R_1$ is a toxic metabolite extractable from the pyrimidine ring by thymidylate synthase; and wherein $R_1$ is selected from the group consisting of —Br, —I, —O-alkyl, —O-aryl, O-heteroaryl, —S-alkyl, —S-aryl, —S-heteroaryl, —CN, —OCN, —SCN, —NH$_2$, —NH-alkyl, —N(alkyl)$_2$, —NHCHO, —NHOH, —NHO-alkyl, NH$_2$CONHO—, NHNH$_2$, and —N$_3$; and wherein Q is selected from the group consisting of sugar groups, thio-sugar groups carbocyclic groups, and salts thereof.

6. The method of claim 5, wherein Q is a furanosyl group of the formula:

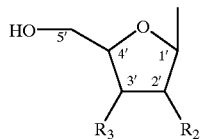

wherein $R_2$ and $R_3$ are the same or different and are independently H or —OH.

7. The method of claim 5, wherein Q is θ-D-ribofuranosyl group of the formula:

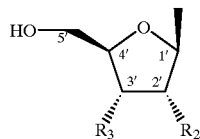

wherein $R_2$ and $R_3$ are the same or different and are independently H— or —OH.

8. The method of claim 1 or 5, wherein the hyperproliferative cell is characterized by the endogenous overexpression of thymidylate synthase as a result of resistance to chemotherapy.

9. The method of claim 1 or 5, wherein the hyperproliferative cell is characterized as resistant to a chemotherapeutic drug.

10. The method of claim 1 or 5, wherein the hyperproliferative cell is characterized as having an inactivated tumor suppressor function.

11. The method of claim 1 or 5, wherein the thymidylate synthase is amplified as a result of selection in vivo by chemotherapy.

12. The method of claim 2 or 5, wherein the endogenous overexpression of thymidylate synthase is the result of amplification of the gene coding for thymidylate synthase.

* * * * *